United States Patent [19]

Achard et al.

[11] Patent Number: 5,484,804
[45] Date of Patent: Jan. 16, 1996

[54] PERHYDROISOINDOLE DERIVATIVES AS ANTAGONISTS OF SUBSTANCE P

[75] Inventors: Daniel Achard, Thiais; Serge Grisoni, Choisy-le-Roi; Jean-Luc Malleron, Marcoussis; Jean-Francois Peyronel, Palaiseau; Michel Tabart, Paris, all of France

[73] Assignee: Rhone-Poulenc Rorer S.A., Antony, France

[21] Appl. No.: 313,121

[22] PCT Filed: Apr. 8, 1993

[86] PCT No.: PTC/FR93/00352

§ 371 Date: Oct. 11, 1994

§ 102(e) Date: Oct. 11, 1994

[87] PCT Pub. No.: WO93/21155

PCT Pub. Date: Oct. 28, 1993

[30] Foreign Application Priority Data

Apr. 10, 1992 [FR] France .................... 9204390

[51] Int. Cl.$^6$ .......................... A61K 31/40; C07D 401/06
[52] U.S. Cl. .................. 514/414; 514/307; 514/314;
514/339; 514/363; 514/365; 514/372; 514/374;
514/378; 514/383; 514/397; 514/416; 546/148;
546/174; 548/181; 548/214; 548/236; 548/247;
548/267.8; 548/312.1; 548/455; 548/470
[58] Field of Search ...................... 514/414, 416,
514/307, 383, 397; 548/470, 455, 312.1,
181; 546/148

[56] References Cited

U.S. PATENT DOCUMENTS 4,042,707  8/1977  Ripka ...................... 548/515

FOREIGN PATENT DOCUMENTS 429366  5/1991  European Pat. Off. .
514273  11/1992  France .

OTHER PUBLICATIONS

McMurry, J. Organic Chemistry, Monterey, Calif., Brooks/Cole Publishing Co., 1984, pp. 642–644, QD251.2M43.

*Primary Examiner*—Jacqueline Haley
*Attorney, Agent, or Firm*—Finnegan, Henderson, Farabow, Garrett & Dunner

[57] ABSTRACT

This invention relates to novel perhydroisoindole derivatives of general formula (I),

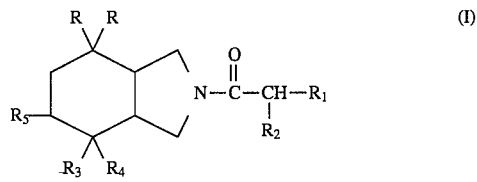

wherein radicals R are phenyl radicals optionally 2- or 3-substituted by a halogen atom or a methyl radical; $R_1$ is optionally substituted phenyl, cyclohexadienyl, naphthyl, indenyl or optionally substituted heterocyclyl; $R_2$ is H, halogen, OH, alkyl, aminoalkyl, alkylaminoalkyl, dialkylaminoalkyl, alkyloxy, alkylthio, acyloxy, carboxy, optionally substituted alkyloxycarbonyl, benzyloxycarbonyl, amino or acylamino; $R_3$ is optionally 2-substituted phenyl; $R_4$ is OH or fluorine when $R_5$ is H, or $R_4$ and $R_5$ are OH or $R_4$ and $R_5$ together form a bond; isomeric forms and mixtures thereof; optionally salts thereof where applicable; and preparation thereof. The novel derivatives are particularly useful as P substance antagonists.

5 Claims, No Drawings

PERHYDROISOINDOLE DERIVATIVES AS ANTAGONISTS OF SUBSTANCE P

FIELD OF THE INVENTION

The present invention relates to new perhydroisoindole derivatives of the general formula:

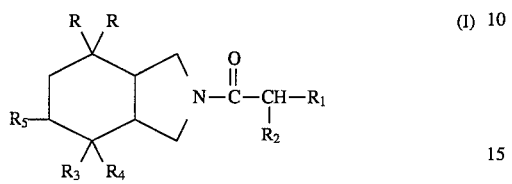

and to their salts, where these exist, which antagonize he effects of substance P and as a result are of particular interest in therapeutic fields where this substance is known to be involved.

BACKGROUND OF THE INVENTION

European Patent Application EP 429 366 has described antagonists of substance P having the structure:

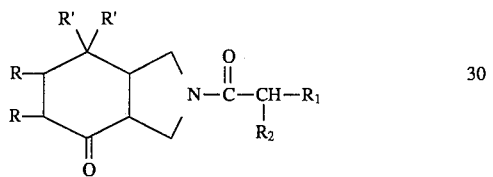

in which the symbols R are hydrogen or together form a bond, the symbols R' are optionally substituted phenyl radicals and the symbols $R_1$ and $R_2$ represent various substitutions. However, these perhydroisoindolone derivatives have been found to be active mainly in binding tests using rat brain homogenates, and display less activity in binding tests using cultures of human lymphoblast cells.

U.S. Pat. No. 4,042,707 had described products derived from isoindole, of the general formula:

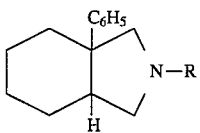

having an opiate activity. These products do not have any activity against substance P.

To date, in spite of research carried out and in spite of the abovementioned interest [M. R. Hanley, TINS, (5) 139 (1982)], no product which acts specifically on substance P and has a nonpeptide structure had been discovered in practice, and for this reason the isoindole derivatives of the general formula (I) are of considerable interest.

DESCRIPTION OF THE INVENTION

In the general formula (I):

the symbols R are identical and represent phenyl radicals which are optionally substituted by a halogen atom or by a methyl radical in position 2 or 3, the symbol $R_1$ represents a phenyl radical which is optionally substituted by one or more halogen atoms or hydroxyl radicals, alkyl radicals which may be optionally substituted (by halogen atoms or amino, alkylamino or dialkylamino radicals), alkyloxy radicals or alkylthio radicals which may be optionally substituted [by hydroxyl radicals, amino radicals, alkylamino radicals or dialkylamino radicals which are optionally substituted (by phenyl, hydroxyl or amino radicals), or dialkylamino radicals, the alkyl parts of which, with the nitrogen atom to which they are attached, form a heterocycle having 5 to 6 chain members which may contain another heteroatom chosen from oxygen, sulphur or nitragen and optionally substituted by an alkyl, hydroxyl or hydroxyalkyl radical)], or is substituted by amino radicals, alkylamino radicals or dialkylamino radicals, the alkyl parts of which, with the nitrogen atom to which they are attached, may form a heterocycle as defined above, or represents a cyclohexadienyl radical, naphthyl radical, indenyl radical or mono- or polycyclic, saturated or unsaturated, heterocyclyl radical containing 5 to 9 carbon atoms and one or more heteroatoms chosen from oxygen; nitrogen or sulphur, which is optionally substituted by a halogen atom or by an alkyl or alkyloxy radical, the symbol $R_2$ represents a hydrogen or halogen atom or a hydroxyl, alkyl, aminoalkyl, alkylaminoalkyl, dialkylaminoalkyl, alkyloxy, alkylthio, acyloxy, carboxyl, alkyloxycarbonyl, dialkylaminoalkyloxycarbonyl, benzyloxycarbonyl, amino or acylamino radical, the symbol $R_3$ represents a phenyl radical which is optionally substituted in position 2 by an alkyl or alkyloxy radical containing 1 or 2 carbon atoms and the symbol $R_4$ represents a fluorine atom or a hydroxyl radical and the symbol $R_5$ represents a hydrogen atom, or the symbols $R_4$ and $R_5$ represent hydroxyl radicals, or the symbol $R_4$ forms a bond with $R_5$.

It is understood that the alkyl or acyl radicals mentioned above contain (unless mentioned specifically) 1 to 4 carbon atoms in a straight or branched chain.

If R carries a halogen substituent, this may be chosen from chlorine or fluorine.

If $R_1$ contains a halogen atom, this may be chosen from chlorine, bromine, fluorine or iodine.

If $R_1$ represents a mono- or polycyclic, saturated or unsaturated, heterocyclyl radical, it may be chosen from, by way of example, thienyl, furyl, pyridyl, dithiinyl, indolyl, isoindolyl, benzothienyl, thiazolyl, isothiazolyl, oxazolyl, imidazolyl, pyrrolyl, triazolyl, thiadiazolyl, quinolyl, isoquinolyl and naphthyridinyl.

If $R_1$ represents phenyl which is substituted by a chain carrying a heterocycle, this can be chosen from pyrrolidinyl, morpholino, piperidinyl, tetrahydropyridinyl, piperazinyl or thiomorpholino.

Furthermore, the products of the general formula (I) have various stereoisomer forms, and it is understood that the racemic forms and the stereoisomer forms having the structure:

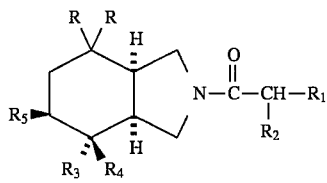

(Ia)

as well as their mixtures, fall within the context of the present invention. More specifically, the perhydroisoindole derivatives in which $R_4$ is hydroxyl or fluorine and $R_5$ is hydrogen, in the (3aS,4S,7aS) form in the pure state, or in the form of the racemic mixture (3aRS,4RS,7aRS), the perhydroisoindole derivatives in which $R_4$ and $R_5$ are hydroxyl, in the (3aS,4S, 5S,7aS) form in the pure state, or in the form of the racemic mixture (3aRS,4RS,5RS,7aRS), and the perhydroisoindole derivatives in which $R_4$ forms a bond with $R_5$, in the (3aS,7aR) form in the pure state, or in the form of the racemic mixture (3aRS,7aSR), fall within the context of the present invention. Moreover, if the symbol $R_2$ is other than the hydrogen atom, the substituted chain on the isoindole has a chiral centre, and it is understood that the (R) or (S) stereoisomer forms and their mixtures form part of the present invention.

The perhydroisoindole derivatives of the general formula (I) can be obtained according to the invention by action of the acid of the general formula:

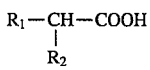

(II)

or a reactive derivative of this acid, in which $R_1$ and $R_2$ are as defined above, on an isoindole derivative of the general formula:

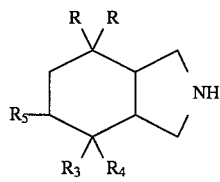

(III)

in which the symbols R, $R_3$, $R_4$ and $R_5$ are as defined above, and if appropriate subsequent conversion of the product obtained in which $R_4$ is a hydroxyl radical and $R_5$ is a hydrogen atom into a product in which $R_4$ is a fluorine atom and $R_5$ is a hydrogen atom or into a product in which $R_4$ and $R_5$ together form a bond.

It is understood that the amino, alkylamino or Carboxyl radicals contained in $R_1$ and/or $R_2$ are preferably protected beforehand. Protection is carried out by any compatible group, the introduction and removal of which do not affect the remainder of the molecule. In particular, the operation is carried out by the methods described by T. W. Greene, Protective Groups in Organic Synthesis, A. Wiley - Interscience Publication (1981), or by McOmie, Protective Groups in Organic Chemistry, Plenum Press (1973).

By way of example,, amino or alkylamino groups can be protected by methoxycarbonyl, ethoxycarbonyl, t-butoxycarbonyl, allyloxycarbonyl, vinyloxycarbonyl, trichloroethoxycarbonyl, trichloroacetyl, trifluoroacetyl, chloroacetyl, trityl, benzhydryl, benzyl, allyl, formyl or acetyl radicals or by the benzyloxycarbonyl radical or its substituted derivatives;

acid groups can be protected by methyl, ethyl, t-butyl, benzyl, benzhydryl or substituted benzyl radicals.

Moreover, if $R_2$ represents a hydroxyl radical, this radical is preferably protected beforehand. The protection is carried out, for example, by an acetyl, trialkylsilyl or benzyl radical, in the form of a carbonate by a —COORa radical, in which Ra is an alkyl or benzyl radical, or in the form of the ketone.

It is also understood that the stereochemistry of the isoindole derivative of the general formula (III) is like that described above for the derivatives of the general formula (I).

In the case of condensation of a reactive derivative of the acid of the general formula (II), this is advantageously carried out by means of the acid chloride, the anhydride, a mixed anhydride or a reactive ester, in which the ester residue is a succinimido, optionally substituted 1-benzotriazolyl, 4-nitrophenyl, 2,4-dinitrophenyl, pentachlorophenyl or phthalimido radical.

The reaction is generally carried out at a temperature of between −40° and +40° C. in an organic solvent such as a chlorinated solvent (dichloromethane, dichloroethane or chloroform, for example), a hydrocarbon (toluene, for example), an ether (tetrahydrofuran or dioxane, for example), an ester (ethyl acetate, for example), an amide (dimethylacetamide or dimethylformamide, for example) or a ketone (acetone, for example), or in a mixture of these solvents, in the presence of an acid acceptor, such as an organic nitrogenous base, such as, for example, pyridine, dimethylaminopyridine, N-methylmorpholine or a trialkylamine (in particlar triethylamine), or such as an epoxide (propylene oxide, for example). It is also possible to carry out the reaction in the presence of a condensing agent, such as a carbodiimide [for example dicyclohexylcarbodiimide or 1- (3-dimethylamino-propyl)-3-ethylcarbodiimide], N,N'-carbonyldiimidazole or 2-ethoxy-1-ethoxycarbonyl-1,2dihydroquinoline, or in an aqueous organic medium, in the presence of an alkaline condensing agent, such as sodium bicarbonate.

In the case of the alternative where a perhydroisoindole derivative of the general formula (I) in which $R_4$ is a hydroxyl radical and $R_5$ is a hydrogen atom was obtained and where a perhydroisoindole derivative in which $R_4$ is a fluorine atom and $R_5$ is a hydrogen atom is desired, the preparation is carried out by fluorination of the derivative obtained above.

The reaction is advantageously carried out by means of a fluorinating agent, such as a sulphur fluoride [morpholinosulphur trifluoride, sulphur tetrafluoride (J. Org. Chem., 40, 3808 (1975)), diethylaminosulphur trifluoride (Tetrahedron, 44, 2875 (1988)), or phenylsulphur trifluoride (J. Am. Chem. Soc., 84, 3058 (1962)], such as selenium tetrafluoride (J. Am. Chem. Soc., 96, 925 (1974) or such as tetrafluorophenylphosphorane (Tet. Let., 907 (1973), using an organic solvent such as a chlorinated solvent (dichloromethane or dichloroethane, for example), at a temperature of between −30° and 30° C.

In the case of the alternative where a perhydroisoindole derivative of the general formula (I) in which $R_4$ is a hydroxyl radical and $R_5$ is a hydrogen atom was obtained and where a perhydroisoindole derivative in which $R_4$ and $R_5$ together form a bond is desired, the preparation is carried out by any known method of dehydration of alcohols which does not detrimentally change the remainder of the molecule. In particular, the dehydration is carried out in an acid medium, for example by the action of a sulphonic acid (p-toluenesulphonic acid and the like), sulphuric acid, phosphoric acid, phosphorus pentoxide or aluminium oxide, or by the action of a hydrochloric acid/acetic acid or hydrobromic acid/acetic acid mixture, at a temperature of between 25° C. and the reflux temperature of the reaction mixture.

Isoindole derivatives of the general formula (I) in which $R_5$ is other than the hydroxyl radical can also be obtained according to the invention by action of an organometallic compound of the general formula: in which $R_3$ is as defined as above and M represents lithium or a $CeX_2$ or MgX radical, in which X is a halogen atom, on a perhydroisoindolone derivative of the general formula:

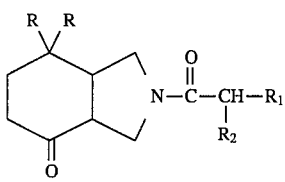

in which R, $R_1$ and $R_2$ are as defined above, and, if appropriate, subsequent conversion of the alcohol of the general formula (I) obtained into a perhydroisoindole derivative in which $R_4$ is a fluorine atom and $R_5$ is a hydrogen atom or into a perhydroisoindole derivative in which $R_4$ and $R_5$ together form a bond.

The reaction is carried out in an anhydrous medium under the usual conditions for reaction of organometallic compounds with a ketone which do not affect the remainder of the molecule. In particular, the reaction is carried out in an ether (for example tetrahydrofuran or ethyl ether), if appropriate in the presence of anhydrous cerium chloride, at a temperature of between −78° and 30° C.

The subsequent operations of conversion into a derivative of the general formula (I) in which $R_4$ is a fluorine atom and $R_5$ is hydrogen or in which $R_4$ and $R_5$ together form a bond are carried out under the conditions described above.

The acids of the general formula (II) can be prepared by the methods described below in the examples, by the methods described in Patent Application EP 429 366 or by a method analogous to these methods.

The perhydroisoindole derivative of the general formula (III) in which $R_4$ and $R_5$ together form a bond can be obtained by dehydration of the corresponding perhydroisoindole derivative in which $R_4$ is a hydroxyl radical and $R_5$ is a hydrogen atom.

The reaction is carried out under the conditions described above for the preparation of derivatives of the general formula (I) in which $R_4$ and $R_5$ together form a bond starting from the corresponding perhydroisoindole derivative in which $R_4$ is a hydroxyl radical and $R_5$ is a hydrogen atom.

The isoindole derivative of the general formula (III) in which $R_4$ is a fluorine atom and $R_5$ is a hydrogen atom can be prepared by fluorination of an isoindole derivative of the general formula:

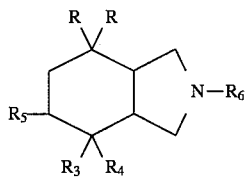

in which R and $R_3$ are as defined above, $R_6$ is a protective radical, $R_4$ is a hydroxyl radical and $R_5$ is a hydrogen atom, and subsequent removal of the protective radical $R_6$.

The protective radical $R_6$ can be any aminoprotective group which is compatible with the reaction and whose introduction and removal does not detrimentally change the remainder of the molecule. Examples which may be mentioned are the alkyloxycarbonyl, benzyloxycarbonyl, optionally substituted benzyl, formyl, chloroacetyl, trichloroacetyl, trifluoroacetyl, vinyloxycarbonyl, phenoxycarbonyl, 1-chloroethoxy-carbonyl or chlorocarbonyl groups.

If preparation of a fluorinated perhydroisoindole derivative of the general formula (III) is desired, the fluorination is carried out under the conditions described above for fluorination of a derivative of the general formula (I) in which $R_4$ is hydroxyl, at a temperature of between −30° and +30° C.

The subsequent removal of the protective radical $R_6$ is carried out by the usual methods. In particular, by the methods described by T. W. Greene, by A. Wiley or by McOmie in the abovementioned references.

The perhydroisoindole derivative of the general formula (III) or (VI) in which $R_4$ is a hydroxyl radical and $R_5$ is a hydrogen atom or a hydroxyl radical can be obtained by the action of an organometallic compound of the general formula (IV) on the corresponding perhydroisoindolone derivative of the general formula:

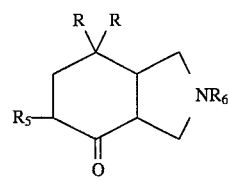

in which R and $R_6$ are as defined above and $R_5$ is a hydrogen atom or an optionally protected hydroxyl radical, and subsequent liberation of the protective radical of $R_5$ and, if appropriate, removal of the protective radical $R_6$.

The reaction is carried out under conditions analogous to those described for preparation of the perhydroisoindole of the general formula (I) starting from the corresponding perhydroisoindolone. It is understood that, depending on the nature of the protective radical of the radical $R_5$, this may be removed simultaneously with the reaction.

The perhydroisoindole derivative of the general formula (VI) can be prepared by protection of the amino of the corresponding derivative of the general formula (III).

The protection is carried out by the usual methods. In particular, in accordance with the abovementioned references.

The perhydroisoindolone derivative of the general formula (VII) in which $R_5$ is a hydrogen atom can be prepared by a method analogous to that described in European Patent Application EP 429 366. The perhydroisoindolone derivative of the general formula (VII) in which $R_5$ is a hydroxyl radical which has been protected beforehand can also be prepared by a method analogous to this method, or as described below in the examples.

The preparation of the perhydroisoindolone derivative of the general formula (V) is carried out by a method analogous to that described in European Patent Application EP 429 366.

It is understood that the perhydroisoindole derivatives of the general formula (I), (III), (V), (VI) and (VII) have several stereoisomer forms. If preparation of a product of the general formula (I) in the (3aS,7aS) form is desired, separation of the isomer forms is preferably carried out on the derivative of the general formula (VII) or on another intermediate carrying an oxo radical in position 4. It can also be carried out on the derivative of the general formula (III). The separation is carried out by any known method which is compatible with the molecule.

By way of example, the separation can be carried out by preparation of an optically active salt, by action of L(+)- or D(−)-mandelic acid or of dibenzoyltartaric or ditoluoyltartaric acid, and subsequent separation of the isomers by crystallization. The isomer required is liberated from its salt in a basic medium.

The new isoindole derivatives of the general forula (I) can be purified, where appropriate, by physical methods, such as crystallization or chromatography.

Where appropriate, the new derivatives of the general formula (I) in which the symbols $R_1$ and/or $R_2$ contain amino or alkylamino substituents can be converted into acid addition salts. Examples which may be mentioned of addition salts with pharmaceutically acceptable acids are the salts formed with inorganic acids (hydrochlorides, hydrobromides, sulphates, nitrates or phosphates) or with organic acids (succinates, fumarates, tartrates, acetates, propionates, maleates, citrates, methanesulphonates, p-toluenesulphonates or isethionates, or with substitution derivatives of these compounds).

The new isoindole derivatives of the general formula (I) can also be converted, where appropriate, if $R_2$ represents a carboxyl radical, into metal salts or addition salts with a nitrogenous base by methods which are known per se. These salts can be obtained by action of a metal base (for example an alkali metal or alkaline-earth metal base), ammonia or an amine on a product according to the invention in a suitable solvent, such as an alcohol, an ether or water, or by an exchange reaction with a salt of an organic acid. The salt formed precipitates, if appropriate after concentration of the solution, and is separated off by filtration, decantation or lyophilization. Examples of pharmaceutically acceptable salts which may be mentioned are the salts with alkali metals (sodium, potassium or lithium) or with alkaline-earth metals (magnesium or calcium), the ammoniumsalt or the salts with nitrogenous bases (ethanolamine, diethanolamine, trimethylamine, triethylamine, methylamine, propylamine, diisopropylamine, NN-dimethylethanolamine, benzylamine, dicyclohexylamine, N-benzyl-β-phenethylamine, NN'-dibenzylethylenediamine, diphenylenediamine, benzhyldrylamine, quinine, choline, arginine, lysine, leucine or dibenzylamine).

The new isoindole derivatives according to the present invention which antagonize the effects of substance P can be used in the fields of analgesia, of inflammation of asthma or of allergies, on the central nervous system, on the cardiovascular system, as an antispasmodic or on the immune system, and also in the field of stimulation of lachrymal secretions.

In fact, the products according to the invention demonstrate an affinity for substance P receptors at doses of between 10 and 1000 nM in accordance with the adapted techniques of D. G. Payan et al., J. of immunology, 133 (6), 3260-5 (1984): Stereospecific receptors for substance P on cultured human IM-9 lymphoblasts and of McPherson et al., J. Pharmacol. Meth., 14, 213 (1985): Analysis of radioligand binding experiments.

It has furthermore been demonstrated that the effect is an antagonistic effect on substance P by means of various products. In the technique described by S. Rosell et al., Substance P, Ed. by US Von Euler and B. Pernow, Raven Press, New York (1977), pages 83 to 88, the products studied demonstrate antagonism of contractions of the guinea-pig ilium induced by substance P or contractions of the guinea-pig ilium induced by septide in concentrations of 6 to 1000 nM.

Substance P is known to be implicated in a certain number of pathological areas:

Agonists and antagonists of substance P, A. S. Dutta Drugs of the future, 12 (8), 782 (1987);

Substance P and pain: an updating, J. L. Henry, TINS, 3(4), 97 (1980);

Substance P in inflammatory reactions and pain, S. Rosell, Actual. Chim. Ther., 12th series, 249 (1985)

Effects of Neuropeptides on Production of Inflammatory Cytokines by Human Monocytes, M. Lotz et al., Science, 241, 1218 (1988).

Neuropeptides and the pathogenesis of allergy, Allergy, 42, 1 to 11 (1987);

Substance P in Human Essential Hypertension, J. Cardiovascular Pharmacology, 10 (suppl. 12), 5172 (1987).

The study of some isoindole derivatives of the general formula (I) by the technique of A. Saria et al., Arch. Pharmacol., 324, 212–218 (1983) adapted for the guinea-pig has made it possible to demonstrate an inhibiting effect on the increase in capillary permeability caused by septide (agohist of substance P), which is evidence of an antiinflammatory activity:

| Product studied | $ED_{50}$ |
| --- | --- |
| Example 1 | 0.04 mg/kg i.v. |
|  | 3.5 mg/kg p.o. |

Injection of substance P in animals causes hypotension. The products studied by the technique of C. A. Maggi et al., J. Auton. Pharmac., 7, 11–32 (1987) demonstrate an antagonistic effect with respect to this hypotension in the guinea-pig. The $ED_{50}$, the dose which reduces by 50% the hypotension induced by an i.v. injection of 250 ng/kg of substance P, is determined.

| Product of the general formula (I) | $ED_{50}$ mg/kg i.v. |
| --- | --- |
| Example 1 | 0.15 |

Injection of substance P causes a bronchospasm in the animal. The bronchoconstriction induced in vivo in the guinea-pig by injection of substance P or a selective agonist of substance P:. [$Pro^9$] substance P, is studied by the technique of H. Konzett and R. Rosseler, Archiv. Exp. Path. Pharmak., 195, 71–74 (1940). This bronchoconstriction is inhibited by injection of a product according to the invention, which is evidence of an antiasthmatic activity. The $ED_{50}$, the dose which reduces by 50% the bronchospasm induced by 3 µg/kg i.v. of [$Pro^9$] substance P, is determined. In this technique, the $ED_{50}$ of the product of Example 1 is 0.7 mg/kg i.v.

Furthermore, in the formalin pain test in the guinea-pig, the product of Example 1 administered perorally 1 hour before the test demonstrates an $ED_{50}$ of 11 mg/kg.

Finally, the isoindole derivatives according to the present invention show no toxicity and they are found to be atoxic in the mouse when administered intravenously in a dose of of 10 mg/kg or subcutaneously in a dose of 40 mg/kg subcutaneously.

Products of the general formula (I) which are of particular interest are those in which:

the symbols R are identical and represent phenyl radicals, the symbol $R_1$ represents a phenyl radical which is optionally substituted by one or more hydroxyl, alkyloxy or dialkylamino radicals, naphthyl radical, indenyl radical or mono- or polycyclic heterocyclyl radical chosen from thienyl, indolyl and benzothienyl and optionally substituted by a halogen atom or by an alkyl or alkyloxy radical, the symbol $R_2$ represents a hydrogen atom or a hydroxyl, alkyl or amino radical, the symbol $R_3$ represents a phenyl radical which is optionally substituted in position 2 by an alkyl or alkyloxy radical containing 1 or 2 carbon atoms and the symbol $R_4$ represents a fluorine atom or a hydroxyl radical and the symbol $R_5$ represents a hydrogen atom, or the symbols $R_4$ and $R_5$ represent hydroxyl radicals, or the symbol $R_4$ forms a bond with $R_5$.

Among these products, those which are of more specific interest are:

7,7-diphenyl-4-(2-methoxyphenyl)-2-[2-(2-methoxyphenyl)propionyl] perhydroisoindol-4-ol;
7,7-diphenyl-4-(2-methoxyphenyl)-2-[2-(2-methoxyphenyl)propionyl] perhydroisoindole-4,5-diol; 7,7-diphenyl-4-(2-methoxyphenyl)-2-[2-(2-hydroxyphenyl)acetyl] perhydroisoindol-4-ol; 7,7-diphenyl-4-(2-methoxyphenyl)-2-(3-indolylacetyl)-perhydroisoindole-4,5-diol;
7,7-diphenyl-4-(2-methoxyphenyl)-2-[(2-methoxyphenyl)acetyl] perhydroisoindol-4-ol; 7,7-diphenyl-4-(2-methoxyphenyl)-2-[2-(2-hydroxyphenyl)propionyl] perhydroisoindol-4-ol;

in the racemic form, in the abovementioned stereoisomer forms or in the form of a mixture.

EXAMPLES

The following examples given nonlimitatively illustrate the present invention.

In the examples which follow, it is understood that, unless mentioned specifically, the proton NMR spectra were recorded at 250 MHz in dimethyl sulphoxide; the chemical shifts are expressed in ppm.

Example 1

0.025 g of 1-hydroxybenzotriazole, 0.38 g of (S)-2-(2-methoxyphenyl)propionic acid and 0.32 cm$^3$ of diisopropylethylamine are added to a suspension of 0.8 g of (3aS,4S,7aS)-7,7-diphenyl-4-(2-methoxyphenyl)-perhydroisoindol-4-ol hydrochloride in 60 cm$^3$ of dry dichloromethane, this solution is then cooled to +5° C. and a suspension of 0.43 g of 1-(3-dimethylaminopropyl)-3-ethylcarbodiimide hydrochloride in 10 cm$^3$ of dry dichloromethane is quickly added. The reaction mixture is stirred at +5° C. for 2 hours and at room temperature for 2 hours, washed with 20 cm$^3$ of water and then washed with 20 cm$^3$ of an aqueous saturated solution of sodium chloride (twice), dried over magnesium sulphate and concentrated to dryness under reduced pressure (2.7 kPa). The residue is chromatographed on a Merck silica gel column (particle size 0.04–0.06 mm, diameter 2.8 cm, height 20 cm) by eluting under a pressure of 0.5 bar of nitrogen with a mixture of cyclohexane and ethyl acetate (80/20 by volume) and collecting fractions of 25 cm$^3$. Fractions 9 to 15 are combined and then concentrated to dryness under reduced pressure (2.7 kPa). The residue is crystallized in a mixture of acetonitrile and diisopropyl ether. 0.17 g of (3aS,4S,7aS)-7,7-diphenyl- 4-(2-methoxyphenyl)-2-[(S)-2-(2methoxyphenyl)propionyl] perhydroisoindol-4-ol is obtained in the form of white crystals which melt at 244° C.

(3aS,4S,7aS)-7,7-Diphenyl-4-(2-methoxyphenyl)perhydroisoindol-4-ol hydrochloride can be prepared in the following manner:

100 cm$^3$ of a 5.2N solution of hydrochloric acid in dioxane are added to a solution of 7.63 g of (3aS,4S,7aS)-7,7-diphenyl-4-(2-methoxyphenyl)-2-tert-butoxycarbonylperhydroisoindol-4-ol in 66 cm$^3$ of dioxane at room temperature. The reaction mixture is stirred at this temperature for 1 hour and then concentrated to dryness under reduced pressure (2.7 kPa). The residue is washed with acetonitrile, filtered off and then dried. 4.88 g of (3aS,4S,7aS)-7,7-diphenyl-4-(2-methoxyphenyl)perhydroisoindol-4-ol hydrochloride are obtained in the form of white crystals which melt at 271° C. (Maquenne block).

(3aS,4S,7aS)-7,7-Diphenyl-4-(2-methoxyphenyl)-2-tert-butoxycarbonylperhydroisoindol-4ol can be prepared in the following manner:

A suspension of 2-methoxyphenylmagnesium bromide (prepared starting from 75.3 g of 2-bromoanisole and 9.8 g of magnesium) in 100 cm$^3$ of dry tetrahydrofuran is added dropwise while stirring to a suspension of 20 g of (3aS,7aS)-7,7-diphenyl-2-tert-butoxycarbonylperhydroisoindol-4-one and 31.6 g of anhydrous cerium chloride in 250 cm$^3$ of dry tetrahydrofuran at room temperature. The reaction mixture is stirred at room temperature for 24 hours, treatea with 400 cm$^3$ of an aqueous saturated solution of ammonium chloride, diluted with 200 cm$^3$ of ethyl acetate, washed with 300 cm$^3$ of water (twice) and then with 300 cm$^3$ of an aqueous saturated solution of sodium chloride, dried over magnesium sulphate, filtered and concentrated to dryness under reduced pressure (2.7 kPa). The residue is chromatographed on a Merck silica gel column (particle size 0.04–0.06 mm, diameter 5.8 cm, height 26.5 cm) by eluting under a pressure of 0.5 bar of nitrogen with a mixture of cyclohexane and ethyl acetate (80/20 by volume) and collecting fractions of 100 cm$^3$. Fractions 9 to 29 are combined and concentrated to dryness under reduced pressure (2.7 kPa). 17.82 g of (3aS,4S,7aS)-7,7-diphenyl-4-(2- methoxyphenyl)-2-tert-butoxycarbonylperhydroisoindol-4-ol are obtained in the form of a white foam.

Proton NMR spectrum (DMSO de): 1.36 (s, 9H, —C(CH$_3$)$_3$); 1.54 (dmt, J=14, 1H, equatorial H of —CH$_2$— in 5); 2.3 (dmt, J=14, 1H, equatorial H of —CH$_2$— in 6); 2.34 (td, J=14 and 2.5, 1H, axial H of —CH$_2$— in 5); 3.07 (td, J=14 and 2.5, axial H of —CH$_2$— in 6); 3.49 (s, 3H, —OCH$_3$); 2.6 to 3.6 (mt, other —CH$_2$— and —CH); 6.85 to 7.7 (mt, 14H, aromatic).

(3aS,7aS)-7,7-Diphenyl-2-tert-butoxycarbonylperhydroisoindol-4-one can be obtained in the following manner:

34.3 cm$^3$ of triethylamine, 58.6 g of di-tert-butyl dicarbonate and then 2.98 g of 4-dimethylaminopyridine are added to a suspension of 80 g of (3aS,7aS)-7,7-diphenylperhydroisoindol-4-one hydrochloride in 400 cm$^3$ of dry dichloromethane at room temperature, while stirring. The reaction mixture is stirred at room temperature for 24 hours, washed with 100 cm$^3$ of an aqueous solution of citric acid, subsequently with 100 cm$^3$ of an aqueous solution of sodium bicarbonate and then with 100 cm$^3$ of an aqueous saturated solution of sodium chloride, dried over magnesium sulphate and concentrated to dryness under reduced pressure (2.7 kPa). 106.5 g of (3aS,7aS)-7,7-diphenyl-2-tert-butoxycarbonylperhydroisoindol-4-one are obtained in the form of an orange foam.

Proton NMR spectrum (DMSO d$_6$): 1.4 (s, 9H, —C(CH$_3$)$_3$); 2.11 (td, J=15 and 7.5, 1H, axial H of —CH$_2$— in 5); 2.3 (dt, J=15 and 3.5, 1H, equatorial H of —CH$_2$— in 5); 2.75 to 2.9 (mt, 4H, —CH$_2$— in 6 and —CH$_2$— in 1); 3.26 (dd, J=7.5 and 7, 1H, —CH in 3a); 3.35 (dd, J=11 and 7, 1H, 1H of —CH$_2$— in 3); 3.97 (mt, 1H, —CH in 7a); 4.1 (d, J=11, 1H, the other H of —CH$_2$— in 3); 7.1 to 7.7 (mt, 10H, aromatic).

(3aS,7aS)-7,7-Diphenylperhydroisoindol-4-one hydrochloride can be obtained in the following manner:

50 cm$^3$ of aqueous 4N sodium hydroxide solution are added slowly to a suspension of 20 g of (3aRS,7aRS)-7,7-diphenylperhydroisoindol-4-one hydrochloride in 250 cm$^3$ of ethyl acetate, while stirring; stirring is continued until the starting material has disappeared. The organic solution is washed with 100 cm$^3$ of distilled water and with 100 cm$^3$ of a saturated solution of sodium chloride, dried over magnesium sulphate and filtered. A solution of 9.3 g of D-(−)-mandelic acid in 50 cm$^3$ of ethyl acetate is added to the solution thus obtained, while stirring. The crystals formed are filtered filtered off, washed with 50 cm$^3$ of ethyl acetate (twice) and dried. The crystals are taken up in a solution of 220 cm$^3$ of acetonitrile and 60 cm$^3$ of distilled water and the mixture is refluxed for 15 minutes, while stirring; the crystals formed are filtered off and crystallized again in a mixture of 100 cm$^3$ of acetonitrile and 35 cm$^3$ of distilled water. 6.4 g of (3aS,7aS)-7,7-diphenylperhydroisoindol-4-one D-mandelate are obtained.

50 cm$^3$ of aqueous 1N sodium hydroxide solution are added to 6.4 g of (3aS,7aS)-7,7-diphenylperhydroisoindol-4-one D-mandelate dissolved in 100 cm$^3$ of ethyl acetate; the reaction mixture is stirred at room temperature until the starting material has disappeared; the organic solution is washed with 50 cm$^3$ of distilled water and with 50 cm$^3$ of a saturated aqueous solution of sodium chloride, dried over magnesium sulphate and filtered; it is acidified by addition of 2 cm$^3$ of a 9N solution of hydrochloric acid in ethanol, while stirring; the crystals obtained are filtered off, washed with ethyl acetate and then with isopropyl ether and dried. 4.24 g of (3aS,7aS)-7,7- diphenylperhydroisoindol-4-one hydrochloride are obtained in the form of white crystals which melt at 270° C. with decomposition.

(S)-2-(2-Methoxyphenyl)propionic acid can be prepared by a method analogous to those described by D.A Evans et al., Tetrahedron, 44, 5525, (1988), in accordance with the following operating method:

1.52 g of lithium hydroxide are added to a solution, cooled to +5° C., of 4.1 g of (4S,5S)-4-methyl- 5-phenyl-3-[(S)-2-(2-methoxyphenyl)propionyl]-oxazolidin-2-one in 60 cm$^3$ of tetrahydrofuran and 30 cm$^3$ of water. The reaction mixture is stirred at this temperature for 3 hours and, after returning to room temperature, ethyl acetate is subsequently added, the mixture is decanted, the aqueous phase is acidified with an aqueous 1N solution of hydrochloric acid and extracted with ethyl acetate and the organic phase is dried over magnesium sulphate and concentrated to dryness under reduced pressure (2.7 kPa). The solid obtained is recrystallized from hexane, filtered off and dried. 0.4 g of (S)-2-(2-methoxyphenyl)propionic acid is obtained in the form of white crystals which melt at 102° C. [α]$_D^{20}$=+84.6° (c=1; CHCl$_3$).

(4S,5S)-4-Methyl-5-phenyl-3-[(S)-2-(2-methoxyphenyl)propionyl] oxazolidin-2-one can be obtained in the following manner:

19.1 g of sodium 1,1,1,3,3,3-hexamethyldisilazanate are added to a solution, cooled to −50° C., of 10 g of (4S,5S)-4-methyl-5-phenyl-3-[(2-methoxyphenyl)acetyl] oxazolidin-2-one in 150 cm$^3$ of tetrahydrofuran, the mixture is stirred at this temperature for 45 minutes and 7.72 cm$^3$ of methyl iodide are then added. The reaction mixture is then stirred at room temperature for 15 hours, subsequently diluted with ethyl acetate, washed with 50 cm$^2$ of water and then with 50 cm$^3$ of an aqueous saturated solution of sodium chloride, dried over magnesium sulphate and concentrated to dryness under reduced pressure (2.7 kPa). The residue obtained is crystallized in isopropyl ether, filtered off and dried. 4.2 g of (4S,5S)-4-methyl-5-phenyl-3-[(S)-2-(2-methoxyphenyl)propionyl] oxazolidin-2-one are obtained in the form of a white solid.

(4S,5S)-4-Methyl-5-phenyl-3-(2-methoxyphenylacetyl)oxazolidin- 2-one can be obtained in the following manner:

9.38 g of 2-methoxyphenylacetic acid are added to a suspension of 1.89 [lacuna] of sodium hydride (80% strength dispersion in liquid paraffin) in 200 cm$^3$ of dry tetrahydrofuran at room temperature. This suspension is cooled to −30° C., 7.77 cm$^3$ of pivaloyl chloride are added, and a solution, cooled to −78° C., obtained by adding a solution of 35.27 cm$^3$ of 1.6M butyllithium in hexane to a solution, cooled to −78° C., of 10 g of (4S,5S)-4-methyl-5-phenyloxazolidin-2-one in 200 cm$^3$ of dry tetrahydrofuran, is then finally added. The reaction mixture is stirred at −30° C. for 45 minutes and then, after returning to room temperature, 200 cm$^3$ of an aqueous saturated solution of ammonium chloride and then 500 cm$^3$ of ethyl acetate are added; after separation by settling, the organic phase is washed twice with 100 cm$^3$ of water and then twice with 100 cm$^3$ of an aqueous saturated solution of sodium chloride, and is dried over magnesium sulphate and concentrated to dryness under reduced pressure (2.7 kPa). The residue is chromatographed on a silica gel column (particle size 0.04–0.06 mm, diameter 4.8 cm, height 36 cm) by eluting under a pressure of 0.6 bar of nitrogen with a mixture of cyclohexane and ethyl acetate (85/15 and then 80/20 by volume) and collecting fractions of 50 cm$^3$. Fractions 14 to 31 are combined and concentrated to dryness under-reduced pressure (2.7 kPa). 13.6 g of (4S,5S)-4-methyl-5-phenyl-3-(2-methoxyphenylacetyl)oxazolidin-2-one are obtained in the form of a yellow oil.

Example 2

By working in accordance with the operating method of Example 22 below, starting from 0.68 g of (3aS,4S,7aS)-7,7-diphenyl-4-(2-methylphenyl)perhydroisoindol- 4-ol hydrochloride and 0.28 cm$^3$ of phenylacetyl chloride, 0.4 g of (3aS,4S,7aS)-7,7-diphenyl-4-(2-methylphenyl)-2-phenylacetylperhydroisoindol-4-ol is obtained in the form of white crystals which melt at 208° C.

(3aS,4S,7aS)-7,7-Diphenyl-4-(2-methylphenyl)perhydroisoindol-4-ol hydrochloride can be prepared in the following manner:

By working in accordance with Example 1, starting from 1.2 g of (3aS,4S,7aS)-7,7-diphenyl-4-(2-methylphenyl)-2-tert-butoxycarbonylperhydroisoindol-4-ol, 0.68 g of (3aS,4S,7aS)-7,7-diphenyl-4-(2-methylphenyl)perhydroisoindol-4-ol hydrochloride is obtained.

Infrared spectrum (KBr), characteristic bands (cm$^{-1}$):
3325, 3100-3000, 3000-2850, 3000-2300, 1600, 1585, 1560, 1495, 1445, 750, 700.

(3aS,4S,7aS)-7,7-Diphenyl-4-(2-methylphenyl)- 2-tert-butoxycarbonylperhydroisoindol-4-ol can be prepared in the following manner:

By working in accordance with the operating method of Example 1, starting from 3 g of (3aS,7aS)- 7,7-diphenyl-2-tert-butoxycarbonylperhydroisoindol-4-one and a suspension of 2-methylphenylmagnesium bromide (prepared starting from 4.6 cm$^3$ of 2-bromotoluene and 0.93 g of magnesium in 15 cm$^3$ of anhydrous tetrahydrofuran), 1.5 g of (3aS,4S,7aS)-7,7-diphenyl-4-( 2-methylphenyl)-2-tert-butoxycarbonylperhydroisoindol-4-ol are obtained in the form of an oil which is used as such in the following test.

Example 3

0.35 cm$^3$ of triethylamine and then 0.33 cm$^2$ of phenylacetyl chloride are added to a suspension of 1.1 g of (3aRS,4RS,7aRS)-7,7-diphenyl-4-(2-methoxyphenyl)perhydroisoindol-4-ol hydrochloride in 25 cm$^3$ of dry dichloromethane at room temperature. The reaction mixture is stirred at this temperature for 24 hours, diluted with 200 cm$^3$ of dichloromethane, washed with 100 cm$^3$ of a saturated solution of sodium bicarbonate, with 100 cm$^3$ of water (twice) and then with an aqueous saturated solution of sodium chloride, dried over magnesium sulphate, filtered and concentrated to dryness under reduced pressure (2.7 kPa). The residue is chromatographed on a Merck silica gel column (particle size 0.04–0.06 mm, diameter 2 cm, height 22 cm) by eluting under a nitrogen pressure of 50 kPa with a mixture of cyclohexane and ethyl acetate (55/45 by volume) and collecting fractions of 20 cm$^3$. Fractions 11 to 18 are combined and concentrated to dryness under reduced pressure (2.7 kPa). The residue obtained is crystallized from 70 cm$^3$ of acetonitrile and the crystals are filtered off and dried. 0.5 g of (3aRS,4RS,7aRS)-7,7-diphenyl-4-(2-methoxyphenyl)-2-(phenylacetyl)perhydroisoindol-4-ol is obtained in the form of a white solid.

Proton NMR spectrum (DMSO d$_6$): 1.5 (dmt, J=14, 1H, equatorial 1H of —CH$_2$— in 5); 2.26 (dmt, J=14, 1H, equatorial H of —CH$_2$— in 6); 2.31 (td, J=14 and 3, 1H, axial H of —CH$_2$— in 5); 2.85 (mt, 1H, —CH< in 3a); 3.02 (td, J=14 and 2.5, 1H, axial H of —CH$_2$— in 6); 3.2 to 3.6 (unresolved peak, —CH$_2$— and CH<); 3.44 (s, 3H, —OCH$_3$); 6.8 to 7.6 (mt, 19H aromatic).

Infrared spectrum (KBr), characteristic bands (cm$^{-1}$): 3100-3000, 3000-2850, 2840, 1640, 1600, 1580, 1495, 1450, 1245, 1030, 750, 720, 700.

(3aRS,4RS,7aRS)-7,7-Diphenyl-4-(2-methoxyphenyl)perhydroisoindol-4 -ol hydrochloride can be prepared in the following manner:

By working in accordance with the operating method of Example 1, starting from 2.7 g of (3aRS,4RS,7aRS)-7,7-diphenyl-4-(2-methoxyphenyl)-2-tert-butoxycarbonylperhydroisoindol-4-ol, 1.77 g of (3aRS,4RS,7aRS)-7,7-diphenyl-4-(2-methoxyphenyl)perhydroisoindol-4-ol hydrochloride are obtained in the form of a white solid.

Proton NMR spectrum (DMSO de): 1.55 (broad d, J=14, 1H, equatorial H of —CH$_2$- in 5); 2.34 (td, J=14 and 2.5, 1H, axial H of —CH$_2$— in 5); 2.37 (broad d, J=14, 1H, equatorial H of —CH$_2$— in 6); 2.52 (mt, 1H of —CH$_2$— in 1); 2.93 (td, J=14 and 2.5; 1H, axial H of —CH$_2$— in 6); 3 to 3.3 (mt, 3H, -CH$_2$— in 3 and the other H of —CH$_2$— in 1); 3.42 (s, 3H, —OCH$_3$—); 3.4 to 3.7 (mt, 2H, —CH< in 3a and 7a); 5.3 (broad unresolved peak, 1H, —OH); 6.8 to 7.7 (mt, 14H, aromatic).

(3aRS,4RS,7aRS)-7,7-Diphenyl-4-(2-methoxyphenyl)-2-tert-butoxycarbonylperhydroisoindol-4ol can be obtained in the following manner:

By working in accordance with the operating method of Example 1, starting from 2.75 g of (3aRS,7aRS)-7,7-diphenyl-2-tert-butoxycarbonylperhydroisoindol-4-one, 1.73 g of anhydrous cerium chloride and a suspension of 2-methoxyphenylmagnesium bromide (obtained starting from 6.57 g of 2-bromoanisole and 0.84 g of magnesium), 2.72 g of (3aRS,4RS,7aRS)-7,7-diphenyl-4-(2-methoxyphenyl)-2-tert-butoxycarbonylperhydroisoindol-4-ol are obtained in the form of a white foam.

Proton NMR spectrum (DMSO d$_6$): At room temperature, a mixture of the rotamers is obtained: 1.3 and 1.35 (mt, 1H, 1H of —CH$_2$— in 5); 2.15 to 2.4 (mt, 2H, the other H of —CH$_2$— in 5 and 1H of —CH$_2$— in 6); 2.5 to 3.6 (mt, —CH$_2$— and —CH<); 3.35 and 3.39 (2s, 3H, —OCH$_3$); 4.68 and 4.72 (2s, 1H, —OH); 6.8 to 7.7 (mt, 14H aromatic).

(3aRS,7aRS)-7,7-Diphenyl-2-tert-butoxycarbonylperhydroisoindol-4-one can be prepared in the following manner:

4.3 cm$^3$ of triethylamine, 7.4 g of di-tertbutyl dicarbonate and then 0.37 g of 4-dimethylaminopyridine are added to a suspension of 10 g of (3aRS,7aRS)-7,7-diphenylperhydroisoindol-4-one hydrochloride in 50 cm$^3$ of dry dichloromethane at room temperature, while stirring. The reaction mixture is stirred at room temperature for 24 hours, washed with 150 cm$^3$ of an aqueous solution of citric acid, subsequently with 100 cm$^3$ of an aqueous solution of sodium bicarbonate and then with 100 cm$^3$ of an aqueous saturated solution of sodium chloride, and is dried over magnesium sulphate and concentrated to dryness under reduced pressure (2.7 kPa). 11 g of (3aRS,7aRS)- 7,7-diphenyl-2-tert-butoxycarbonylperhydroisoindol-4-one are obtained in the form of a cream foam.

Proton NMR spectrum (DMSO de): 1.38 (s, 9H, —C(CH$_3$)$_3$); 2.08 (td, J=14 and 6, 1H, axial H of —CH$_2$— in 5); 2.28 (dmt, 1H, equatorial H of —CH$_2$— in 5); 2.7 to 2.85 (mt, 4H, —CH$_2$— 1 and —CH$_2$— in 6); 3.27 (mt, 2H, —CH< in 3a and 1H of —CH$_2$— in 3); 3.9 to 4.05 (mt, 2H, —CH< in 7a and the other H of —CH$_2$— in 3); 7.1 to 7.7 (mt, 10H aromatic).

Example 4

0.025 g of 1-hydroxybenzotriazole, 0.27 cm$^3$ of (S)-2-phenylpropanoic acid and 0.32 cm$^3$ of diisopropylethylamine are added to a suspension of 0.8 g of (3aS,4S,7aS)-7,7-diphenyl-4-(2-methoxyphenyl)perhydroisoindol-4-ol hydrochloride in 80 cm$^3$ of dry dichloromethane, this solution is then cooled to +5° C. and a suspension of 0.43 g of 1-(3-dimethylaminopropyl)-3-ethylcarbodiimide hydrochloride in 10 cm$^3$ of dry dichloromethane is quickly added. The reaction mixture is stirred at +5° C. for 2 hours and at room temperature for 18 hours, washed with 20 cm$^3$ of water and then washed with 20 cm$^3$ of an aqueous saturated solution of sodium chloride (twice), and is dried over magnesium sulphate and concentrated to dryness under reduced pressure (2.7 kPa). The residue is chromatographed on a Merck silica gel column (particle size 0.04–0.06 mm, diameter 2.8 cm, height 20 cm) by eluting under a pressure of 0.5 bar of nitrogen with a mixture of cyclohexane and ethyl acetate (65/35 by volume) and collecting fractions of 25 cm$^3$. Fractions 6 to 12 are combined and then concentrated to dryness under reduced pressure (2.7 kPa). The residue is triturated in diisopopyl ether. 0.53 g of (3aS,4S,7aS)- 7,7-diphenyl-4-(2-methoxyphenyl)-2-[(S)-2-phenylpropionyl] perhydroisoindol-4-e is obtained in the form of white crystals which melt with decomposition at 128° C.

Example 5

0.024 g of 1-hydroxybenzotriazole and 0.33 g of (S)-2-acetyloxy-2-phenylacetic acid are added to a suspension of 0.75 g of (3aS,4S,7aS)-7,7-diphenyl-4-(2-methoxyphenyl)perhydroisoindol-4-ol hydrochloride in 60 cm$^3$ of dry dichloromethane, this solution is then cooled to +5° C. and a suspension of 0.4 g of 1-(3-dimethylaminopropyl)-3- ethylcarbodiimide hydrochloride in 20 cm³ of dry dichloromethane is quickly added, followed by a solution of 0.63 cm³ of diisopropylethylamine in 20 cm³ of dry dichloromethane. The reaction mixture is stirred at +5° C. for 2 hours and at room temperature for 24 hours, diluted with 120 cm³ of dichloromethane, washed with 100 cm³ of water and then with 100 cm³ of an aqueous saturated solution of sodium chloride, and is dried over magnesium sulphate and concentrated to dryness under reduced pressure (2.7 kPa). The residue is chromatographed on a Merck silica gel column (particle size 0.04–0.06 mm, diameter 2.5 cm, height 39 cm) by eluting under a pressure of 0.5 bar of nitrogen with a mixture of cyclohexane and ethyl acetate (50/50 by volume) and collecting fractions of 60 cm³. Fractions 6 to 10 are combined and then concentrated to dryness under reduced pressure (2.7 kPa). 0.96 g of (3aS,4S,7aS)-7,7-diphenyl-4-(2-methoxyphenyl)-2-[(S)-2-acetyloxy-2-phenylacetyl]perhydroisoindol-4-ol is obtained in the form of a white foam.

Proton NMR spectrum (DMSO d6): At room temperature, a mixture of the two rotamers is found: 1.25 (dmt, J=14, equatorial H of —CH₂— in 5); 1.4 (dmt, J=14, equatorial H of —CH₂— in 5); 2.01 (s, 3H, —OCOCH₃); 2.27 (mt, 2H, H of —CH₂— in 5 and 1H of —CH₂— in 6); 2.65 to 3.6 (mt, —CH₂— and —CH<); 3.22 (s, 3H, —OCH₃); 4.38 (s, OH of one rotamer); 4.86 (s, OH of the other rotamer); 5.66 (s, —CO—CH—O of one rotamer); 5.88 (s, —CO—CH—O of the other rotamer); 6.6 to 7.6 (mt, 19H aromatic).

Infrared spectrum (KBr), characteristic bands (cm⁻¹): 3400, 3100-3000, 3000-2850, 2830, 1740, 1660, 1600, 1580, 1495, 1450, 1235, 1050, 755, 700.

1.4 cm3 of an aqueous 1N solution of sodium hydroxide and then 10 cm³ of water are added to a solution of 0.8 g of (3aS,4S,7aS)-7,7-diphenyl-4-(2- methoxyphenyl)-2-[(S)-2-acetyloxy-2-phenylacetyl]perhydroisoindol-4-ol in 30 cm³ of ethanol. The reaction mixture is refluxed for 1 hour and concentrated to dryness under reduced pressure (2.7 kPa), and the residue is taken up in 50 cm³ of water and then 1.5 cm³ of an aqueous 1N solution of hydrochloric acid and extracted with 40 cm³ of ethyl acetate (3 times). The organic phases are combined, washed with 50 cm³ of water, dried over magnesium sulphate and concentrated to dryness under reduced pressure (2.7 kPa). The residue is chromatographed on a Merck silica gel column (particle size 0.04–0.06 mm, diameter 2.5 cm, height 27 cm) by eluting under a pressure of 0.4 bar of nitrogen with a mixture of cyclohexane and ethyl acetate (50/50 by volume) and collecting fractions of 30 cm³. Fractions 2 to 5 are combined and concentrated to dryness under reduced pressure (2.7 kPa). The residue is triturated in isopropyl ether. 0.6 g of (3aS,4S,7aS)-7,7-diphenyl-4-(2-methoxyphenyl)-2-[(S)-2-hydroxy-2-phenylacetyl]perhydroisoindol-4-ol is obtained in the form of white crystals which melt at 256° C.

Example 6

By working in accordance with Example 4, starting from 2.25 g of (3aS,4S,7aS)-7,7-diphenyl-4-(2-methoxyphenyl)perhydroisoindol-4-ol hydrochloride and 1.25 g of (S)-2-tert-butoxycarbonylamino-2-phenylacetic acid, 0.35 g of (3aS,4S,7aS)-7,7-diphenyl-4-(2-methoxyphenyl)- 2-[(S)-2-tert-butoxycarbonylamino-2-phenylacetyl]perhydroisoindol-4-ol is obtained in the form of a white foam.

Proton NMR spectrum (DMSO d₆): At room temperature, a mixture of the rotamers is found: 1.3 and 1.4 (2s, —C(CH₃)₃); 1.3 to 1.7 (mt, 1H of —CH₂— in 5); 2.15 to 2.45 (mt, 2H, the other H of —CH₂— in 5 and one H of —CH₂— in 6); 2.7 to 3.7 (mt, —CH₂— and —CH<); 3.33 and 3.4 (2s, —OCH₃); 4.84 and 5.11 (2s, 1H of NCO-CH-N of the two isomers); 6.6 to 7.7 (mt, 19H aromatic).

Infrared spectrum (KBr), characteristic bands (cm⁻¹): 3580, 3550-3450, 3420, 3100-3000, 3000-2850, 2835, 1710, 1645, 1600, 1580, 1490, 1455, 1395, 1370, 1240, 1170, 1030.

By working in accordance with Example 1, starting from 0.62 g of (3aS,4S,7aS)-7,7-diphenyl-4-(2-methoxyphenyl)-2-[(S)-2-tert-butoxycarbonylamino-2-phenylacetyl] perhydroisoindol-4-ol, 0.54 g of (3aS,4S,7aS)-7,7-diphenyl-4-(2-methoxyphenyl)-2-[(S)-2-amino-2-phenylacetyl] perhydroisoindol-4-ol hydrochloride is obtained in the form of a white foam.

Proton NMR spectrum (DMSO de): A mixture of diastereoisomers is found: 1.34 and 1.53 (2dmt, J=14, 1H in total, equatorial H of —CH₂— in 5 for the two isomers); 2.31 (mt, 2H, the other H of —CH₂— in 5 and 1H of —CH₂— in 6); 2.8 to 3.7 (mt, —CH₂— and —C<); 3.36 and 3.42 (2s, 3H, —OCH₃); 4.76 and 4.95 (2s, 1H, NCO-CH-N of the two isomers); 6.6 to 7.7 (mt, 19H aromatic).

Infrared spectrum (KBr), characteristic bands (cm⁻¹): 3425, 3100-3000, 3000-2850, 2830, 3150-2500, 1660, 1600, 1585, 1495, 1450, 1235, 1030, 755, 700.

Example 7

0.28 g of carbonyldiimidazole is added to a solution of 0.28 g of (2-methoxyphenyl)acetic acid in 20 cm³ of dry dichloromethane. The mixture is stirred at room temperature for 1 hour and a suspension of 0.7 g of (3aS,4S,7aS)-4,7,7-triphenylperhydroisoindol-4-ol hydrochloride in 20 cm³ of dry dichloromethane and then 0.48 cm³ of triethylamine are subsequently added in succession. The reaction mixture is stirred at room temperature for 24 hours, diluted with 100 cm³ of dichloromethane, washed with 100 cm³ of water (twice) and then with 100 cm³ of an aqueous saturated solution of sodium chloride, dried over magnesium sulphate and concentrated to dryness under reduced pressure (2.7 kPa). The residue is chromatographed on a Merck silica gel column (particle size 0.04–0.06 mm, diameter 2 cm, height 16 cm) by eluting under a pressure of 0.5 bar of nitrogen with a mixture of cyclohexane and ethyl acetate (55/45 by volume) and collecting fractions of 20 cm³. Fractions 7 to 8 are combined and then concentrated to dryness under reduced pressure (2.7 kPa). The residue is crystallized in 16 cm³ of acetonitrile. The crystals are filtered off and dried. 0.3 g of (3aS,4S,7aS)-4,7,7-triphenyl-2-(2-methoxyphenyl)acetylperhydroisoindol-4-ol is obtained in the form of white crystals which melt at 236° C.

(3aS,4S,7aS)-4,7,7-Triphenylperhydroisoindol-4-ol hydrochloride can be prepared in the following manner:

115 cm³ of a 6.3N solution of hydrochloric acid in dioxane are added to a solution of 6.8 g of (3aS,4S,7aS)-4,7,7-triphenyl-2-tert-butoxycarbonylperhydroisoindol-4-ol in 60 cm³ of dioxane at room temperature. The reaction mixture is stirred at this temperature for 2 hours and then concentrated to dryness under reduced pressure (2.7 kPa). The residue is washed with acetonitrile, filtered off and then dried. 4 g of (3aS,4S,7aS)-4,7,7-triphenylperhydroisoindol-4-ol hydrochloride are obtained in the form of a white foam.

Proton NMR spectrum (DMSO d₆): 1.51 (td, J=14, 1H, axial H of —CH₂— in 5); 1.72 (broad d, J=14, 1H, equatorial H of —CH₂— in 5); 2.34 (broad d, J=14, 1H, equatorial H of —CH₂— in 6); 2.42 (td, J=10, 1H of —CH₂— in 1); 2.87 (td, J=14, 1H, axial H of —CH₂— in 6); 2.94 (mt, 1H, —CH< in 3a); 3.05 to 3.25 (mt, 3H, the other H of —CH₂— in 1 and the —CH₂— in 3); 3.57 (mt, 1H, —CH< in 7a); 5.67 (unresolved peak, 1H, OH); 7.1 to 7.6 (mt, 15H aromatic); 8.9 (2 unresolved peaks, each 1H, $NH_2^+$).

Infrared spectrum (KBr), characteristic bands (cm⁻¹): 3500-3250, 3100-3000, 3000-2825, 2800-2250, 1600, 1580, 1495, 1445, 1075, 750, 700.

(3aS,4S,7aS)-4,7,7-Triphenyl-2-tert-butoxycarbonylperhydroisoindol-4-ol can be prepared in the following manner:

A suspension of 10.78 g of phenylmagnesium bromide in 65 cm³ of diethyl ether is added dropwise to a solution of 11.66 g of (3aS,7aS)-7,7-diphenyl-2-tert-butoxycarbonylperhydroisoindol-4-one in 70 cm³ of dry tetrahydrofuran at room temperature, while stirring. The reaction mixture is stirred at room temperature for 24 hours, refluxed for 5 hours, subsequently treated with 250 cm³ of a saturated aqueous solution of ammonium chloride, diluted with 200 cm³ of ethyl acetate, washed with 200 cm³ of water (twice) and then with 200 cm³ of a saturated aqueous solution of sodium chloride, and is dried over magnesium sulphate, filtered and concentrated to dryness under reduced pressure (2.7 kPa). The residue is chromatographed on a Merck silica gel column (particle size 0.04–0.06 mm, diameter 5.3 cm, height 31.5 cm) by eluting under a pressure of 0.5 bar of nitrogen with a mixture of cyclohexane and ethyl acetate (90/10 by volume) and collecting fractions of 100 cm³. Fractions 23 to 48 are combined and concentrated to dryness under reduced pressure (2.7 kPa). 5.75 g of (3aS,4S,7aS)-4,7,7-triphenyl-2-tert-butoxycarbonylperhydroisoindol-4-ol are obtained in the form of a pale yellow foam.

Proton NMR spectrum (DMSO de): 1.37 (s, 9H, —C(CH₃)₃); 1.65 (mt, 2H, —CH₂— in 5); 2.28 (broad d, J=14, 1H, equatorial H of —CH₂— in 6); 2.65 (t, J=9, 1H of —CH₂— in 1); 2.85 (mt, 1H, —CH< in 3a); 3.05 (td, J=14 and 3.5; 1H, axial H of —CH₂— in 6); 3.25 (mt, 2H, the other H of —CH₂— in 1 and 1H of —CH₂— in 3); 3.4 (d, J=11, 1H, the other H of —CH₂— in 3); 3.5 (mt, 1H, —CH< in 7a); 4.4 (s, 1H, OH); 7.1 to 7.6 (mt, 15H aromatic).

Infrared spectrum (KBr), characteristic bands (cm⁻¹): 3425, 3100-3000, 3000-2850, 1680, 1600, 1580, 1495, 1475, 1410, 1365, 1170, 750, 700.

Example 8

By working in accordance with Example 4, starting from 1.13 g of (3aS,4S,7aS)-7,7-diphenyl-4-(2-methoxyphenyl)perhydroisoindol-4-ol hydrochloride and 0.42 g of (2-methoxyphenyl)acetic acid, 0.61 g of (3aS,4S,7aS)-7,7-diphenyl-4-(2-methoxyphenyl)-2-[(2-methoxyphenyl)acetyl]perhydroisoindol-4-ol is obtained in the form of white crystals which melt at 204° C.

Example 9

By working in accordance with Example 4, starting from 0.75 g of (3aS,4S,7aS)-7,7-diphenyl-4-(2-methoxyphenyl)perhydroisoindol-4-ol hydrochloride and 0.28 g of (3-methoxyphenyl)acetic acid, 0.54 g of (3aS,4S,7aS)-7,7-diphenyl-4-(2-methoxyphenyl)-2-[(3-methoxyphenyl)acetyl] perhydroisoindol-4-ol is obtained in the form of white crystals which melt at 185° C.

Example 10

By working in accordance with Example 4, starting from 0.75 g of (3aS,4S,7aS)-7,7-diphenyl-4-(2-methoxyphenyl)perhydroisoindol-4-ol hydrochloride and 0.28 g of (4-methoxyphenyl)acetic acid, 0.61 g of (3aS,4S,7aS)-7,7-diphenyl-4-(2-methoxyphenyl)-2-[(4-methoxyphenyl)acetyl] perhydroisoindol-4-ol is obtained in the form of white crystals which melt at 211° C.

Example 11

By working in accordance with Example 4, starting from 0.8 g of (3aS,4S,7aS)-7,7-diphenyl-4-(2-methoxyphenyl)perhydroisoindol-4-ol hydrochloride and 0.38 g of 21-naphthylacetic acid, 1.16 g of (3aS,4S,7aS)-7,7-diphenyl-4-(2-methoxyphenyl)-2-(1-naphthylacetyl)perhydroisoindol-4-ol are obtained in the form of a white solid which melts at 225° C.

Example 12

By working in accordance with Example 4, starting from 0.8 g of (3aS,4S,7aS)-7,7-diphenyl-4-(2-methoxyphenyl)perhydroisoindol-4-ol hydrochloride and 0.34 g of 3-thienylacetic acid, 0.53 g of (3aS,4S,7aS)- 7,7-diphenyl-4-(2-methoxyphenyl)-2-[(3-thienyl)acetyl] perhydroisoindol-4-ol is obtained in the form of white crystals which melt with decomposition at 106° C.

Example 13

0.41 g of cabonyldiimidazole is added to a solution of 0.44 g of 3-indolylacetic acid in 20 cm³ of dry dichloromethane. The mixture is stirred at room temperature for 1 hour and a suspension of 1.1 g of (3aRS,4RS,7aRS)-7,7-diphenyl-4-(2-methoxyphenyl)perhydroisoindol-4-ol hydrochloride in 25 cm³ of dry dichloromethane and then 0.7 cm³ of triethylamine are subsequently added in succession. The reaction mixture is stirred at room temperature for 24 hours, diluted with 100 cm³ of dichloromethane, washed with 100 cm³ of water (twice) and then with 100 cm³ of an aqueous saturated solution of sodium chloride, and is dried over magnesium sulphate and concentrated to dryness under reduced pressure (2.7 kPa). The residue is chromatographed on a Merck silica gel column (particle size 0.04–0.06 mm, diameter 2 cm, height 22 cm) by eluting under a pressure of 0.5 bar of nitrogen with a mixture of cyclohexane and ethyl acetate (35/65 by volume) and collecting-fractions of 20 cm³. Fractions 7 to 8 are combined and then concentrated to dryness under reduced pressure (2.7 kPa). The residue is triturated in diisopropylether. 0.17 g of (3aRS,4RS,7aRS)-7,7-diphenyl-2-(3-indolylacetyl)-4-(2-methoxyphenyl)perhydroisoindol-4-ol is obtained in the form of a white solid.

Proton NMR spectrum (DMSO d₆): 1.48 (broad d, J=14.5, 1H, equatorial H of —CH₂— in 5); 2.27 (broad d, J=14.5, 1H, equatorial H of —CH₂— in 6); 2.32 (td, J=14.5 and 2, 1H, axial H of —CH₂— in 5); 3.02 (td, J=14.5 and 2, 1H, axial H of —CH₂— in 6); 2.88 and 3.2 to 3.7 (2 mt, 1H and 5H respectively, —CH₂— and —CH); 3.44 (s, 3H, —OCH₃); 3.52 (s, 2H, —N—COCH₂—); 6.8 to 7.6 (mt, 19H, aromatic).

Infrared spectrum (KBr), characteristic bands (cm⁻¹): 3425, 3125-3000, 3000-2850, 1625, 1585, 1490, 1460, 1235, 1030, 745, 700.

Example 14

A solution of 0.43 g of 2-(3-indolyl)-2-oxoacetyl chloride in 20 cm³ of dry dichloromethane and then a solution of 0.6 cm³ of triethylamine in 5 cm³ of dry dichloromethane are added in succession to a suspension of 0.96 g of (3aS,4S, 7aS)-7,7-diphenyl-4-(2-methoxyphenyl)perhydroisoindol-4-ol hydrochloride in 25 cm³ of dry dichloromethane at room temperature, while stirring. The reaction mixture is stirred at this temperature for 24 hours, subsequently diluted with 200 cm³ of dichloromethane, washed with 100 cm³ of an aqueous 1N solution of sodium hydroxide and with 50 cm³ of an aqueous saturated solution of sodium chloride, and is dried over magnesium sulphate and concentrated to dryness under reduced pressure (2.7 kPa). The residue is chromatographed on a Merck silica gel column (particle size 0.04–0.06 mm, diameter 2.5 cm, height 1 cm) by eluting under a pressure of 0.4 bar of nitrogen with a mixture of 1,2-dichloroethane and methanol (70/30 by volume) and collecting fractions of 15 cm³. Fractions 2 to 9 are combined and concentrated to dryness under reduced pressure (2.7 kPa). 1.15 g of (3aS,4S,7aS)-7,7-diphenyl-2-[2-oxo-2-(3-indolyl)acetyl]-4-(2-methoxyphenyl)perhydroisoindol-4-ol are obtained in the form of an orange foam.

Infrared spectrum (KBr), characteristic bands (cm⁻¹): 3400, 3250, 3100-3000, 3000-2850, 2835, 1650- 1600, 1580, 1520, 1490, 1455, 1235, 1030, 755, 700.

0.38 g of sodium borohydride is added to a solution of 1.1 g of (3aS,4S,7aS)-7,7-diphenyl-2-[(RS)- 2-oxo-2-(3-indolyl)acetyl]-4-(2-methoxyphenyl)perhydroisoindol-4-ol in 35 cm³ of ethanol at room temperature, while stirring. The reaction mixture is stirred at this temperature for 4 hours and then treated with 2 cm³ of acetic acid and concentrated to dryness under reduced pressure (2.7 kPa). The residue is dissolved in 100 cm³ of ethyl acetate and the organic phase is washed with 50 cm³ of an aqueous 0.1N solution of sodium hydroxide, with 50 cm³ of water and then with 50 cm³ of an aqueous saturated solution of sodium chloride, and is dried over magnesium sulphate and concentrated to dryness under reduced pressure (2.7 kPa). The residue is chromatographed on a Merck silica gel column (particle size 0.04–0.06 mm, diameter 2.8 cm, height 27 cm) by eluting under a pressure of 0.4 bar of nitrogen with a mixture of 1,2-dichloroethane and methanol (96/4 by volume) and collecting fractions of 10 cm³. Fractions 17 to 31 are combined and concentrated to dryness under reduced pressure (2.7 kPa). The residue is triturated in diisopropyl ether. 0.45 g of (3aS,4S,7aS)-7,7-diphenyl- 2-[(RS)-2-hydroxy-2-(3-indolyl)acetyl]-4-(2-methoxyphenyl)perhydroisoindol-4-ol is obtained in the form of a white foam.

Proton NMR spectrum (DMSO de): At room temperature, a mixture of isomers and rotamers is found: 1.4 (mt, 1H, equatorial H of —CH₂— in 5); 2.3 (mt, 2H, axial H of —CH₂— in 5 and 1H of —CH2— in 6); 2.5 to 3.8 (mt, —CH₂— and —CH<); 3.30–3.32–3.35 and 3.38 (4s, OCH₃ of the various isomers and rotamers); 5–5.12–5.24 and 5.28 (4s, 1H, >N—CO—CH—O of the various isomers and rotamers); 6.5 to 7.8 (mt aromatic).

Infrared spectrum (KBr), characteristic bands (cm⁻¹): 3420, 3125-3000, 3000-2850, 2830, 1630, 1600, 1580, 1495, 1450, 1235, 1030, 755, 745, 700.

Example 15

By working in accordance with the operating method of Example 4, starting from 0.8 g of (3aS,4S,7aS)-7,7-diphenyl-4-(2-methoxyphenyl)perhydroisoindol-4-ol hydrochloride and 0.39 g of (5-fluoro-3-indolyl)acetic acid, 0.36 g of (3aS,4S,7aS)-7,7-diphenyl-2-[(5-fluoro-3-indolyl)acetyl]-4-(2-methoxyphenyl)perhydroisoindol-4-ol is obtained in the form of white crystals which melt with decomposition at 170° C.

Example 16

By working in accordance with Example 4, starting from 0.8 g of (3aS,4S,7aS)-7,7-diphenyl-4-(2-methoxyphenyl)perhydroisoindol-4-ol hydrochloride and 0.41 g of (5-methoxy-3-indolyl)acetic acid, 0.66 g of (3aS,4S,7aS)-7,7-diphenyl-2-[(5-methoxy-3-indolyl)acetyl] -4-(2-methoxyphenyl)perhydroisoindol-4-ol is obtained in the form of a beige foam.

Proton NMR spectrum (DMSO d₆): 1.5 (broad d, J=14, 1H, equatorial H of —CH₂— in 5); 2.29 (broad d, J=14, 1H, equatorial H of —CH₂— in 6); 2.35 (td, J=14 and 2.5; axial 1H of —CH₂— in 5); 3.04 (td, J=14 and 2.5; axial H of —CH₂— in 6); 2.8 to 3.9 (mt, —CH₂— and —CH<); 3.44 (s, —OCH₃); 3.75 (s, NCO—CH₂—); 3.89 (s, 3H, —OCH₃ of the indole); 6.7 to 7.7 (mt, 18H aromatic); 10.3 (unresolved peak, 1H, NH of the indole).

Infrared spectrum (KBr), characteristic bands (cm⁻¹):3300-2200, 3125-3000, 3000-2850, 2830, 1625, 1600, 1580, 1485, 1450, 1230, 1215, 1025, 755, 700.

Example 17

By working in accordance with Example 4, starting from 0.75 g of (3aS,4S,7aS)-7,7-diphenyl-4-(2-methoxyphenyl)perhydroisoindol-4-ol hydrochloride and 0.32 g of (1-methyl-3-indolyl)acetic acid, 0.56 g of (3aS,4S,7aS)-7,7-diphenyl-4-(2-methoxyphenyl)-2-[(1-methyl-3-indolyl)acetyl)perhydroisoindol-4-ol is obtained in the form of a beige foam.

Proton NMR spectrum (DMSO d₆): At room temperature, a mixture of the two rotamers is found: 1.42 (mt, 1H, 1H of —CH₂— in 5); 2.31 (mt, 2H, the other H of —CH₂— in 5 and 1H of —CH₂— in 6); 2.94 (mt, the other H of —CH₂— in 6); 2.7 to 3.6 (mt, —CH₂— and —CH<); 3.37 (s, 3H, —OCH₃); 3.45 and 3.5 (2s, 2H, —COCH₂Ar); 3.72 and 3.78 (2s, 3H, NCH₃); 6.8 to 7.7 (mt, 19H aromatic).

Infrared spectrum (KBr), characteristic bands (cm⁻¹): 3400, 3125-3000, 3000-2850, 2830, 1637, 1600, 1580, 1485, 1450, 1235, 1050, 750, 700.

Example 18

4.2 cm³ of triethylamine and then 2.4 g of (2-methoxyphenyl)acetic acid chloride in 50 cm³ of dichloromethane are added to a solution of 4.5 g of (3aRS,4RS,5RS,7aRS)-7,7-diphenyl-4-(2-methoxyphenyl)perhydroisoindole-4,5-diol hydrochloride in 100 cm³ of dichloromethane, cooled to 0° C. The reaction mixture is stirred at room temperature for 90 minutes; it is washed with twice 10 cm³ of water, and is dried over magnesium sulphate and concentrated to dryness under reduced pressure (2.7 kPa). The solid which has crystallized is taken up in. 100 cm³ of diisopropyl ether and then filtered off and washed with 50 cm³ of a saturated solution of sodium bicarbonate and then 50 cm³ of diisopropyl ether. 4.35 g of (3aRS,4RS,5RS,7aRS)- 7,7-diphenyl-4-(2-methoxyphenyl)-2-(2-methoxyphenyl)- acetylperhydroisoindole-4,5-diol are obtained in the form of a light beige solid which melts at 278° C.

(2-Methoxyphenyl)acetic acid chloride is obtained starting from a mixture of 2.2 g of (2-methoxyphenyl)-acetic acid and 20 cm³ of thionyl chloride, which is refluxed for 30 minutes. After concentration to dryness under reduced pressure (2.7 kPa), 2.4 g of a yellow oil, which is used in the crude state in the subsequent syntheses, are obtained.

(3aRS,4RS,5RS,7aRS)-7,7-Diphenyl-4-(2-methoxyphenyl)perhydroisoindole-4,5-diol hydrochloride can be prepared in the following manner:

25 cm³ of a 6N solution of hydrochloric acid in dioxane are added to a solution of 5.15 g of (3aRs,4RS,5RS,7aRS)-7,7-diphenyl-4-(2-methoxyphenyl)-2-tert-butoxycarbonylperhydroisoindole-4,5-diol in 25 cm³ of dioxane at room temperature. The reaction mixture is stirred at this temperature for 1 hour and then concentrated to dryness under reduced pressure (2.7 kPa). The residue is washed with 20 cm³ of acetonitrile, filtered off and dried. 4.5 g of (3aRS,4RS,5RS,7aRS)-7,7-diphenyl-4-(2-methoxyphenyl)perhydroisoindole-4,5-diol hydrochloride are obtained in the form of white crystals which melt at a temperature above 300° C.

(3aRS,4RS,5RS,7aRS)-7,7-Diphenyl-4-(2-methoxyphenyl)-2-tert-butoxycarbonylperhydroisoindole- 4,5-diol can be prepared in the following manner:

A suspension of 30.9 g of 2-methoxyphenylmagnesium bromide in 170 cm³ of dry tetrahydrofuran is added dropwise to a suspension of 26.4 g of (3aRS,5RS,7aRs)-5-acetoxy-7,7-diphenyl-4-(2-methoxyphenyl)-2-tert-butoxycarbonylperhydroisoindol-4one and 43.3 g of anhydrous cerium chloride in 265 cm³ of dry tetrahydrofuran at room temperature, while stirring. The reaction mixture is stirred at room temperature for 24 hours, treated with 400 cm³ of an aqueous saturated solution of ammonium chloride, taken up in 1000 cm³ of ethyl acetate and then filtered through Celite. The organic phase is separated by settling, dried over magnesium sulphate, filtered and concentrated to dryness under reduced pressure (2.7 kPa). The residue is chromatographed on a Merck silica gel column (particle size 0.04–0.06 mm, diameter 7 cm, height 55 cm) by eluting under a pressure of 0.5 bar of nitrogen with a mixture of cyclohexane and ethyl acetate (70/10 by volume) and collecting fractions of 250 cm³. Fractions 10 to 19 are combined and concentrated to dryness under reduced pressure (2.7 kPa). 18 g of (3aRS,4RS,5RS,7aRS)-7,7-diphenyl-4-(2-methoxyphenyl)-2-tert-butoxycarbonylperhydroisoindole-4,5-diol are obtained in the form of white crystals which melt at 229° C.

(3aRS,5RS,7aRS)-5-Acetoxy-7,7-diphenyl-2-tert-butoxycarbonylperhydroisoindol-4-one can be prepared in the following Banner:

46.9 cm³ of triethylamine, 11.8 g of di-tert-butyl dicarbonate and then 0.3 g of 4-dimethylaminopyridine are added to a suspension of 19 g of (3aRS,5RS,7aRS)-5-acetoxy-7,7-diphenylperhydroisoindol-4-one hydrochloride in 200 cm³ of dry dichloromethane at a temperature of about 5° C. while stirring. The reaction mixture is stirred at room temperature for 24 hours and then washed with an aqueous saturated solution of sodium bicarbonate. The organic phase is decanted, dried over magnesium sulphate, filtered and concentrated to dryness under reduced pressure (2.7 kPa). The residue is crystallized from 120 cm³ of diisopropyl ether. 21 g of (3aRS,5RS,7aRS)-5-acetoxy-7,7-diphenylperhydroisoindol- 4-one are obtained in the. form of white crystals which melt at 213° C.

(3aRS,5RS,7aRS)-5-Acetoxy-7,7-diphenylperhydroisoindol-4-one hydrochloride can be prepared in the following manner:

394 cm³ of a 5.2N solution of hydrochloric acid in dioxane are added to a solution of 51.2 g of (3aRS,5RS,7aRS)-5-acetoxy-7,7-diphenyl-2-vinyloxycarbonylperhydroisoindolin-4-one in 118 cm³ of dioxane at room temperature. The reaction mixture is stirred at this temperature for 1 hour and then concentrated to dryness under reduced pressure (2.7 kPa). The residue is recrystallized from 200 cm³ of boiling ethanol. 13.4 g of (3aRS,5RS,7aRS)-5-acetoxy- 7,7-diphenylperhydroisoindol-4-one hydrochloride are obtained in the form of white crystals which melt at a temperature above 300° C.

(3aRS,5RS,7aRS)-5-Acetoxy-7,7-diphenyl-2-vinyloxycarbonylperhydroisoindolin-4-one can be prepared in the following manner:

13.6 cm³ of vinyl chloroformate are added to a solution of 58 g of (3aRS,5RS,7aRS)-5-acetoxy-2-benzyl- 7,7-diphenylperhydroisoindolin-4-one in 580 cm³ of dry dichloromethane at room temperature, while stirring. The reaction mixture ismbrought to the reflux temperature of the solvent for one hour, cooled to room temperature and concentrated to dryness under reduced pressure (2.7 kPa). The residue is crystallized from 400 cm³ of a mixture of diisopropyl ether and petroleum ether (50/50 by volume). 51.4 g of (3aRS,5RS,7aRS)-5-acetoxy-7,7-diphenyl-2-vinyloxycarbonylperhydroisoindol-4-one are obtained in the form of yellow crystals which melt at 205°–210° C.

(3aRS,5RS,7aRS)-5-Acetoxy-2-benzyl-7,7-diphenylperhydroisoindol-4-one can be prepared in the following manner:

15 drops of trifluoroacetic acid are added to a solution of 86 g of 6-acetoxy-4,4-diphenyl-2-cyclohexenone and 96 cm³ of N-butoxymethyl-N(trimethylsilylmethyl)benzylamine in 1000 cm³ of dichloromethane. The reaction mixture is stirred at room temperature for 15 hours, 2 g of sodium carbonate are then added and the mixture is concentrated to dryness under reduced pressure (2.7 kPa). The residue is chromatographed on a Merck silica gel column (particle size 0.04–0.06 mm, diameter 7 cm, height 70 cm) by eluting under a pressure of 0.5 bar of nitrogen with a mixture of cyclohexane and ethyl acetate (20/80 by volume) and collecting fractions of 200 cm³. Fractions 6 to 10 are combined and concentrated to dryness under reduced pressure (2.7 kPa). 70 g of (3aRS,5RS,7aRS)-5-acetoxy-2-benzyl-7,7-diphenylperhydroisoindol-4-one are obtained in the form of a honey (melting point below 40° C.).

N-Butoxymethyl-N-(trimethylsilylmethyl)benzylamine can be prepared in accordance with the method of Y. Terao et al., Chem. Pharm. Bull., 33, 2762 (1985).

6-Acetoxy-4,4-diphenyl-2-cyclohexenone can be prepared in accordance with the method described by W. Oppolzer et al., Helv. Chim. Acta, 59, 2012 (1976).

Example 19

By working in accordance with Example 18, starting from 0.5 g of (3AS,4S,5S,7AS)-7,7-diphenyl-4-phenylperhydroisoindole-4,5-diol hydrochloride and 0.39 g of (2-methoxyphenyl)acetic acid, 0.4 g of (3AS,4S,5S,7AS)-7,7-diphenyl-4-phenyl-2-(2-methoxyphenyl)acetylperhydroisoindole-4,5-diol is obtained in the form of a white solid which melts with decomposition at 150° C.

Example 20

By working in accordance with Example 1, starting from 0.5 g of (3AS,4S,5S,7AS)-7,7-diphenyl-4-phenylperhydroisoindole-4,5-diol hydrochloride and 0.25 g of (S)-2-(2-methoxyphenyl)propionic acid, 0.52 g of (3AS,4S,5S,7AS)-7,7-diphenyl-4-phenyl-2-[(S)-2-(2-methoxyphenyl)propionyl] perhydroisoindole-4,5-diol is obtained in the form of a white solid which melts with decomposition at 158° C.

Example 21

0.46 g of 1-(3-dimethylaminopropyl)-3-ethylcarbodiimide and 0.34 cm³ of diisopropylamine are added to a solution of 0.9 g of (3aRS,4RS,5RS,7aRS)-7,7-diphenyl-4-(2-methoxyphenyl)perhydroisoindole-4,5-diol hydrochloride, 0.4 g of 3-indolylacetic acid and 20 mg of 1-hydroxybenzotriazole hydrate in 90 cm³ of dichloromethane, cooled to 0° C. The mixture is stirred at room temperature for 15 hours, acidified with 0.1N HCl and then taken up in an aqueous saturated solution of sodium chloride. The organic phase is decanted, dried over magnesium sulphate and concentrated to dryness under reduced pressure (2.7 kPa). The foam obtained is recrystallized from 10 cm³ of boiling acetonitrile. 0.85 g of (3aRS,4RS,5RS,7aRS)-7,7-diphenyl-4-(2-methoxyphenyl)-2-(3-indolyl)acetylperhydroisoindole-4,5-diol is obtained in the form of a white solid which melts at 266° C.

Example 22

0.1 cm³ of triethylamine and then 0.04 cm³ of phenylacetyl chloride are added to a suspension of 0.14 g of (3AS,4S,7AS)-7,7-diphenyl-4-fluoro-4-(2-methoxyphenyl)perhydroisoindole hydrochloride in 7 cm³ of dry dichloromethane at room temperature. The reaction mixture is stirred at this temperature for 5 hours, diluted with 100 cm³ of dichloromethane, washed with 40 cm³ of a saturated solution of sodium bicarbonate and then with 40 cm³ of water, and is dried over magnesium sulphate and concentrated to dryness under reduced pressure (2.7 kPa). The residue obtained is triturated in diisopropyl ether. 0.1 g of (3AS,4S,7AS)-7,7-diphenyl-4-fluoro-4-(2-methoxyphenyl)-2-phenylacetylperhydroisoindole is obtained in the form of a white foam.

Proton NMR spectrum (DMSO De): At room temperature, a mixture of rotamers is found: 1.62 (mt, 1H, 1H of —CH₂— in 5); 2 to 3.8 (mt, —CH₂— and —CH<); 3.38 and 3.42 (2s, 3H, —OCH₃); 6.7 to 7.6 (mt, 19H, aromatic).

Infrared spectrum (KBr), characteristic bands (cm⁻¹): 3100-3000, 3000-2850, 2840, 1640, 1600, 1580, 1495, 1455, 1240, 1030, 755, 720, 700.

(3AS,4S,7AS)-7,7-Diphenyl-4-fluoro-4-(2methoxyphenyl)perhydroisoindole hydrochloride can be obtained in the following manner:

20 cm³ of a 6.3N solution of hydrochloric acid in dioxane are added to a solution of 2.07 g of (3AS,4S,7AS)-7,7-diphenyl-4-fluoro-4-(2-methoxyphenyl)-2-tert-butoxycarbonylperhydroisoindole in 20 cm³ of dioxane at room temperature. The reaction mixture is stirred at this temperature for 3 hours and then concentrated to dryness under reduced pressure (2.7 kPa). The residue is crystallized in 40 cm³ of absolute ethanol and the crystals are filtered off and then dried. 1 g of (3AS,4S,7AS)-7,7-diphenyl-4-fluoro- 4-(2-methoxyphenyl)perhydroisoindole hydrochloride is obtained in the form of white crystals which melt at 270° C.

(3AS,4S,7AS)-7,7-Diphenyl-4-fluoro-4-(2-methoxyphenyl)-2-tert-butoxycarbonylperhydroisoindole can be obtained in the following manner:

A solution of 4.3 cm³ of diethylaminosulphur trifluoride in 20 cm³ of dry dichloromethane is added dropwise to a solution, cooled to 0° C., of 6.48 g of (3AS,4S,7AS)-7,7-diphenyl-4-(2-methoxyphenyl)-2-tert-butoxycarbonylperhydroisoindol-4-ol in 70 cm³ of dry dichloromethane. The reaction mixture is stirred at this temperature for 3 hours, washed with 100 cm³ of an aqueous saturated solution of sodium bicarbonate and then with 100 cm³ of an aqueous saturated solution of sodium chloride, and is dried over magnesium sulphate and concentrated to dryness under reduced pressure (2.7 kPa). The residue is chromatographed on a Merck silica gel column (particle size 0.04–0.06 mm, diameter 4.8 cm, height 26 cm) by eluting under a pressure of 0.5 bar of nitrogen with a mixture of cyclohexane and ethyl acetate (95/5 by volume) and collecting fractions of 50 cm³. Fractions 34 to 63 are combined and concentrated to dryness under reduced pressure (2.7 kPa). 2.2 g of (3AS,4S,7AS)-7,7-diphenyl-4-fluoro- 4-(2-methoxyphenyl)-2-tert-butoxycarbonylperhydroisoindole are obtained in the form of a white foam.

Example 23

1.5 cm³ of triethylamine and then 1.6 g of (2-methoxyphenyl)acetic acid chloride are added to a solution of 1.5 g of (3AS,7aR)-4,4-diphenyl-7-(2-methoxyphenyl)-2,3,3a,4,5,7a-hexahydroisoindole hydrochloride in 20 cm³ of dichloromethane, cooled to 0° C. The reaction mixture is stirred at room temperature for 15 hours; it is washed with twice 40 cm³ of water, and is dried over magnesium sulphate and concentrated to dryness under reduced pressure (2.7 kPa). The residue is chromatographed on a Merck silica gel column (particle size 0.04–0.06 mm, diameter 3.6 cm, height 25 cm) by eluting under a pressure of 0.5 bar of nitrogen with a mixture of cyclohexane and ethyl acetate (75/25 by volume) and collecting fractions of 25 cm³. Fractions 14 to 28 are combined and concentrated to dryness under reduced pressure (2.7 kPa). The yellow foam obtained is recrystallized from 10 cm³ of cyclohexane to give 0.38 g of (3AS,7aR)-4,4-diphenyl-2-(2-methoxyphenyl)acetyl-7-(2-methoxyphenyl)- 2,3,3a,4,5,7a-hexahydroisoindole in the form of a beige solid which melts at 142° C.

(3AS,7aR)-4,4-Diphenyl-7-(2-methoxyphenyl)- 2,3,3a,4,5,7a-hexahydroisoindole hydrochloride can be obtained in the following manner:

A solution of 8.56 g of (3AS,4S,7AS)-7,7-diphenyl-4-(2-methoxyphenyl)-2-tert-butoxycarbonylperhydroisoindol-4-ol in 53 cm³ of acetic acid and 30 cm³ of 12N hydrochloric acid is heated at 95° C. for 45 minutes, subsequently cooled to room temperature and concentrated to dryness under reduced pressure (2.7 kPa). The residue is recrystallized from 20 cm³ of acetonitrile. 5.2 g of (3AS,7aR)-4,4-diphenyl-7-(2-methoxyphenyl)-2,3,3a,4,5,7a-hexahydroisoindole hydrochloride are obtained in the form of white crystals which melt at a temperature above 300° C., and the product is used in the crude state in the subsequent syntheses.

Example 24

A solution of 1.03 g of (3AS,7AS)-7,7-diphenyl-4-(2-methoxyphenyl)-2-phenylacetylperhydroisoindol-4-ol and 0.95 g of 4-methylphenylsulphonic acid in 50 cm³ of toluene is refluxed for 3 hours. After cooling, the reaction mixture is diluted with 200 cm³ of dichloromethane, washed with 100 cm³ of an aqueous 4N solution of sodium hydroxide (twice), with 100 cm³ of water and then with 100 cm³ of an aqueous saturated solution of sodium chloride, dried over magnesium sulphate and concentrated to dryness under reduced pressure (2.7 kPa). The residue is chromatographed on a Merck silica gel column (particle size 0.04–0.06 mm, diameter 3.5 cm, height 25 cm) by eluting under a pressure of 0.4 bar of nitrogen with a mixture of cyclohexane and ethyl acetate (50/50 by volume) and collecting fractions of 60 cm³.

Fractions 5 to 8 are combined and concentrated to dryness under reduced pressure (2.7 kPa). The residue is triturated in petroleum ether. 0.38 g of (3AS,7aR)-4,4-diphenyl-7-(2-methoxyphenyl)-2-phenylacetyl-2,3,3a,4,5,7a-hexahydro-(1H)-isoindole is obtained in the form of a white foam.

Proton NMR spectrum (DMSO $d_6$): At room temperature, a mixture of the rotamers is found: 2.5 to 3.9 (mt, —$CH_2$— and —CH<); 3.17 and 3.32 (AB, J=12.5 and AB limit, —$COCH_2Ar$); 3.48 and 3.5 (2s, —$OCH_3$); 5.87 (mt, 1H, vinyl H); 6.7 to 7.6 (mt, 19H aromatic).

Infrared spectrum (KBr), characteristic bands (cm$^{-1}$): 3100-3000, 3000-2850, 2840, 1640, 1600, 1580, 1495, 1450, 1245, 1030, 750, 720, 700.

Example 25

By working in accordance with Example 4, but starting from 1 g of (3AS,4S,7AS)-7,7-diphenyl-4-(2-methoxyphenyl)perhydroisoindol-4-ol hydrochloride and 0.37 g of phenylacetic acid, 0.3 g of (3AS,4S,7AS)-7,7-diphenyl-4-(2-methoxyphenyl)-2-phenylacetylperhydroisoindol-4-ol is obtained in the form of white crystals which melt at 192° C.

Example 26

By working in accordance with Example 4, but starting from 1 g of (3AS,4S,7AS)-7,7-diphenyl-4-(2-methoxyphenyl)perhydroisoindol-4-ol hydrochloride and 0.48 g of (2-dimethylaminophenyl)acetic acid, 0.91 g of (3AS,4S,7AS)-7,7-diphenyl-4-(2-methoxyphenyl)-2-[(2-dimethylaminophenyl)acetyl] perhydroisoindol-4-ol is obtained in the form of white crystals which melt at 207° C.

Example 27

By working in accordance with Example 4, but starting from 1 g of (3AS,4S,7AS)-7,7-diphenyl-4-(2-methoxyphenyl)perhydroisoindol-4-ol hydrochloride and 0.48 g of 3-indenylacetic acid, 0.21 g of (3AS,4S,7AS)-7,7-diphenyl-4-(2-methoxyphenyl)-2-[(3-indenyl)acetyl] perhydroisoindol-4-ol is obtained in the form of a white foam.

Proton NMR spectrum (DMSO $d_6$): At room temperature, a mixture of the rotamers is found: 3.35 (2s, 3H of $OCH_3$); 4.82 (1H of OH); 6.1 and 6.4 (1H of the indene); 6.8 to 7.6 (m, 18H of the phenyls and of the indene).

Infrared spectrum (KBr), characteristic bands (cm$^{-1}$): 3410, 3100-3000, 3000-2850, 2830, 1630, 1600, 1580, 1495, 1485, 1450, 1460-1425, 1235, 1025, 755, 755-700.

Example 28

By working in accordance with Example 4, but starting from 2 g of (3AS,4S,7AS)-7,7-diphenyl-4-(2-methoxyphenyl)perhydroisoindol-4-ol hydrochloride and 0.96 g of 3-indolylacetic acid, 2.17 g of (3AS,4S,7AS)- 7,7-diphenyl-4-(2-methoxyphenyl)-2-[(3-indolyl)acetyl] perhydroisoindol-4-ol are obtained in the form of white crystals which melt at 142° C.

Example 29

By working in accordance with Example 4, but starting from 0.8 g of (3AS,4S,7AS)-7,7-diphenyl-4-(2-methoxyphenyl)perhydroisoindol-4-ol hydrochloride and 0.46 g of (3-benzo[b]thienyl)acetic acid, 0.5 g of (3AS,4S,7AS)-7,7-diphenyl-4-(2-methoxyphenyl)-2-[(3-benzo[b]thienyl)acetyl]perhydroisoindol-4-ol is obtained in the form of white crystals which melt at 130° C. with decomposition.

Example 30

By working in accordance with Example 4, but starting from 0.73 g of (3AS,4S,7AS)-7,7-diphenyl-4-(2-methoxyphenyl)perhydroisoindol-4-ol hydrochloride and 0.5 g of (S)-2-(2-benzyloxyphenyl)propionic acid, 0.73 g of (3AS,4S,7AS)-7,7-diphenyl-4-(2-methoxyphenyl)-2-[(S)-2-(2-benzyloxyphenyl)propionyl]perhydroisoindol-4-ol is obtained in the form of a white foam.

Proton NMR spectrum (DMSO $d_6$): At room temperature, a mixture of the rotamers is found: 1.15 (2d, 3H of $CH_3$—CH); 3.35 (2s, 3H of $OCH_3$); 3.98 and 3.78 (2q, 1H of CH—$CH_3$); 4.2 (s, 1H of OH); 4.6 to 5 (2dd, 2H of $CH_2O$); 6.7 to 7.6 (m, 23H aromatic).

0.005 g of 10% strength palladium-on-charcoal is added to a solution of 0.73 g of (3AS,4S,7AS)-7,7-diphenyl-4-(2-methoxyphenyl)-2-[(S)-2-(2benzyloxyphenyl)propionyl] perhydroisoindol-4-ol obtained above in 20 cm$^3$ of absolute ethanol and hydrogen is bubbled into the reaction mixture at room temperature for 2 hours. The reaction mixture is filtered through Celite and then concentrated to dryness under reduced pressure (2.7 kPa). The residue is chromatographed on a Merck silica gel column (particle size 0.04–0.06 mm, diameter 2.4 cm, height 20 cm) by eluting under a pressure of 0.5 bar of nitrogen with a mixture of cyclohexane and ethyl acetate (80/20 by volume) and collecting fractions of 30 cm$^3$. Fractions 3 to 8 are combined and concentrated to dryness under reduced pressure (2.7 kPa). 0.2 g of (3AS,4S,7AS)-7,7-diphenyl-4-(2-methoxyphenyl)-2-[(S)-2-(2hydroxyphenyl)propionyl] perhydroisoindol-4-ol is obtained in the form of white crystals which melt at 150° C. with decomposition.

(S)-2-(2-Benzyloxyphenyl)propionic acid can be prepared in the following manner:

A solution of 1.07 g of (1R,2S)-N-[(S)-2-(2-benzyloxyphenyl)propionyl] -2,10-camphorsultam in a mixture of 0.47 cm$^3$ of an aqueous 30% strength solution of sodium hydroxide and 10 cm$^3$ of tetrahydrofuran is stirred at room temperature for 48 hours. The reaction mixture is concentrated to dryness under reduced pressure (2.7 kPa) and then diluted with 20 cm$^3$ of distilled water, and the aqueous phase is extracted with 25 cm$^3$ of dichloromethane, subsequently acidified with 3 cm$^3$ of an aqueous 37% strength solution of hydrochloric acid and finally extracted 3 times with 25 cm$^3$ of dichloromethane. The organic phase is dried over magnesium sulphate and concentrated to dryness under reduced pressure (2.7 kPa). 0.5 g of (S)-2-(2-benzyloxyphenyl)propionic acid is obtained in the form of a colourless oil.

Proton NMR spectrum (CDCl$_3$): 1.5 (d, 3H of $CH_3$—CH); 4.18 (q, 1H of CH—$CH_3$); 5.1 (2H of $OCH_2$); 6.95 to 7.45 (m, 9H aromatic).

(1R,2S)-N-[(S)-2-(2-Benzyloxyphenyl)propionyl] -2,10-camphorsultamcan be prepared in the following manner:

1.62 g of potassium tert-butoxide are added in fractions to a solution of 4.1 g of (1R,2S)-N-[(2-benzyloxyphenyl)acetyl] -2,10-camphorsultam in 40 cm$^3$ of tetrahydrofuran, cooled to −78° C. and a solution of 2.63 cm$^3$ of methyl iodide in 2 cm$^3$ of tetrahydrofuran is then added dropwise to this suspension. The reaction mixture is stirred at −78° C. for 18 hours and 40 cm$^3$ of an aqueous saturated solution of ammonium chloride is then added. After returning to room temperature, the reaction mixture is extracted with 80 cm$^3$ of ethyl acetate and the organic phase is washed twice with 25 cm$^3$ of an aqueous saturated solution of ammonium chloride, dried over magnesium sulphate and concentrated to dryness under reduced pressure (2.7 kPa). The residue is chromatographed on a Merck silica gel column (particle size 0.04–0.06 mm, diameter 4 cm, height 39 cm) by eluting under a pressure of 0.3 bar of nitrogen with dichloromethane and collecting fractions of 25 cm³. Fractions 21 to 53 are combined and concentrated to dryness under reduced pressure (2.7 kPa). The residue is crystallized from diisopropyl ether. 1.1 g of (1R,2S)-N-[(S)-2-(2benzyloxyphenyl)propionyl] -2,10-camphorsultam are obtained in the form of white crystals which melt at 131° C.

(1R,2S)-N-[(2-Benzyloxyphenyl)acetyl]-2,10-camphorsultam can be prepared in the following manner:

A solution of 0.74 g of sodium hydroxide in 20 cm³ of distilled water is added dropwise to a solution, cooled to +10° C. of 3.23 g of (1R,2S) -2,10-camphorsultam in 16 cm³ of dry dichloromethane, followed by 0.03 cm³ of Aliquat 336®. A solution of 3.9 g of (2methoxyphenyl)acetyl chloride in 5 cm³ of dichloromethane is then added dropwise at +10° C. The reaction mixture is stirred at +10° C. for 1 hour and decanted, the aqueous phase is extracted with 80 cm³ of dichloromethane and the organic phases are combined, washed with 80 cm³ of distilled water, dried over magnesium sulphate and concentrated to dryness under reduced pressure (2.7 kPa). The residue is crystallized from 15 cm³ of diisopropyl ether. 4.1 g of (1R,2S)-N-[ (2-benzyloxyphenyl)acetyl]-2,10-camphorsultam are obtained in the form of white crystals which melt at 116° C.

Example 31

By working in accordance with Example 4, but starting from 12.27 g of 7,7-diphenyl-4-(2-methoxyphenyl)perhydroisoindol-4-ol hydrochloride and 7.88 g of (2-benzyloxyphenyl)acetic acid, 16.4 g of (3AS,4S,7AS)-7,7-diphenyl-4-(2-methoxyphenyl)-2-[(2-benzyloxyphenyl)acetyl] perhydroisoindol-4-ol are obtained in the form of a white foam.

Proton NMR spectrum (DMSO de): At room temperature, a mixture of the rotamers is found: 3.4 (s, 3H of OCH₃); 5 (s, 2H of —CH₂O); 6.85 to 7.5 (m, 23H aromatic).

By working in accordance with Example 30, starting from 16.4 g of (3AS,4S,7AS)-7,7-diphenyl-4-(2-methoxyphenyl)-2-[2-(2-benzyloxyphenyl)acetyl]acetyl]perhydroisoindol-4-ol, 11.4 g of (3AS,4S,7AS)-7,7-diphenyl-4-(2-methoxyphenyl)-2-[2-(2-hydroxyphenyl)acetyl] perhydroisoindol-4-ol are obtained in the form of white crystals which melt at 190° C.

Example 32

0.16 g of 1-hydroxybenzotriazole, 2.59 g of (S)-2-(2-methoxyphenyl)propionic acid and 2.08 cm³ of diisopropylethylamine are added to a suspension of 5 g of (3AS,7AR)-4,4-diphenyl-7-(2-methoxyphenyl)- 2,3,3a,4,5,7a-hexahydro-(1H)-isoindole hydrochloride in 70 cm³ of dry dichloromethane, this solution is subsequently cooled to +5° C. and a suspension of 2.8 g of 1-(3-dimethylaminopropyl)-3-ethylcarbodiimide hydrochloride in 10 cm³ of dry dichloromethane is quickly added. The reaction mixture is stirred at +5° C. for 2 hours and then at room temperature for 24 hours, washed with 20 cm³ of water and then with 20 cm³ of an aqueous saturated solution of sodium chloride (twice), and is dried over magnesium sulphate and concentrated to dryness under reduced pressure (2.7 kPa). The residue is chromatographed on a Merck silica gel column (particle size 0.04–0.06 mm, diameter 4 cm, height 20 cm) by eluting under a pressure of 0.5 bar of nitrogen with a mixture of cyclohexane and ethyl acetate (80/20 by volume) and collecting fractions of 50 cm³. Fractions 2 to 8 are combined and concentrated to dryness under reduced pressure (2.7 kPa). The residue is triturated in diisopropyl ether. 4.43 g of (3AS,7aR)-4,4-diphenyl- 7-(2-methoxyphenyl)-2-[(S)-2-(2-methoxyphenyl)propionyl] -2,3,3a,4,5,7a-hexahydro-(1H)-isoindole are obtained in the form of white crystals which melt at 104° C. with decomposition.

Example 33

30 mg of 1-hydroxybenzotriazole hydrate, 0.66 g of 1-(3-dimethylaminopropyl)-3-ethylcarbodiimide and 0.6 cm³ of diisopropylethylamine are added to a solution of 1.1 g of (3AS,4S,5S,7AS)-7,7-diphenyl-4-(2-methoxyphenyl)perhydroisoindole-4,5-diol and 0.58 g of (S)-2-(2-methoxyphenyl)propanoic acid in 30 cm³ of dichloromethane, cooled to 0° C. The mixture is stirred at room temperature for 3 hours and 30 minutes and 100 cm³ of water and 50 cm³ of an aqueous saturated solution of sodium chloride are added. The organic phase is decanted, dried over magnesium sulphate and concentrated to dryness under reduced pressure (2.7 kPa). The yellow residue obtained is chromatographed on a Merck silica gel column (particle size 0.04–0.06 mm, diameter 2 cm, height 30 cm) by eluting under a nitrogen pressure of 50 kPa with a mixture of cyclohexane and ethyl acetate (60/40 by volume) and collecting fractions of 25 cm³. Fractions 6 to 14 are combined and then concentrated to dryness under reduced pressure (2.7 kPa). 0.9 g of (3AS,4S,5S,7AS)-7,7-diphenyl-4-(2-methoxyphenyl)-2-[S]-2-(2methoxyphenyl)propionyl] perhydroisoindole-4,5-diol which melts at 256° C. is obtained.

(3AS,4S,5S,7AS)-7,7-Diphenyl-4-(2-methoxyphenyl)perhydroisoindole-4,5-diol can be obtained in the following manner:

520 cm³ of water and 70 cm³ of aqueous 1N sodium hydroxide solution are added to 13 g of (3AS,4S,5S,7AS)-7,7-diphenyl-4-(2-methoxyphenyl)perhydroisoindole-4,5-diol 1,4-ditoluoyl-L-tartrate dissolved in 260 cm³ of methanol; the reaction mixture is stirred at room temperature until the starting material has disappeared. The crystals formed are filtered, filtered off and dried. 7.6 g of (3AS,4S,5S,7AS)-7,7-diphenyl-4-(2-methoxyphenyl)perhydroisoindole-4,5-diol which melts at 235° C. are obtained.

(3AS,4S,5S,7AS)-7,7-Diphenyl-4-(2-methoxyphenyl)perhydroisoindole-4,5-diol 1,4-ditoluoyl-L-tartrate can be prepared in the following manner:

29.2 g of (-)-1,4-ditoluoyl-L-tartaric acid are added to a solution of 30 g of (3aRS,4RS,5RS,7aRS)- 7,7-diphenyl-4-(2-methoxyphenyl)perhydroisoindole-4,5-diol in 500 cm³ of methanol, while stirring. After all the solids have dissolved, the reaction mixture is concentrated to dryness under reduced pressure (2.7 kPa); the foam obtained is crystallized from 500 cm³ of ethyl ether. The crystals obtained are recrystallized to a constant optical rotation from a mixture of ethanol and water (60/40 by volume). 13.3 g of (3AS,4S, 5S,7AS)-7,7-diphenyl-4-(2-methoxyphenyl)perhydroisoindole-4,5-diol 1,4-ditoluoyl-L-tartrate which melts at 240° C. are obtained.

(3aRS,4RS,5RS,7aRS)-7,7-Diphenyl-4-(2-methoxyphenyl)perhydroisoindole-4,5-diol can be prepared in the following manner:

A mixture of 2 g of (3aRS,4RS,5RS,7aRS)-2-benzyl-7,7-diphenyl-4-(2-methoxyphenyl)perhydroisoindole-4,5-diol and 50 cm³ of ethanol is heated at 65° C., while stirring; 0.65 g of 20% strength palladium hydroxide-on-charcoal is added and the reaction mixture is then hydrogenated at a temperature of 65° C. and under atmospheric pressure, while stirring. After a reaction time of 1 hour, the theoretical volume of hydrogen was absorbed; the reaction mixture is filtered and then concentrated to dryness under reduced pressure (2.7 kPa). The residue is crystallized from 10 cm³ of isopropyl ether. 1.45 g of (3aRS,4RS,5RS,7aRS)-7,7-diphenyl-4-(2-methoxyphenyl)perhydroisoindole-4,5-diol which melts at 230° C. are obtained.

(3aRS,4RS,5RS,7aRS)-2-Benzyl-7,7-diphenyl-4-(2-methoxyphenyl)perhydroisoindole-4,5-diol can be prepared in the following manner:

A solution of 22 g of (3aRS,5RS,7aRS)-5-acetoxy-2-benzyl-7,7-diphenylperhydroisoindol-4-one in 220 cm³ of tetrahydrofuran is added dropwise to a suspension of 84.4 g of 2-methoxyphenylmagnesium bromide in 1000 cm³ of tetrahydrofuran at room temperature, while stirring. The reaction mixture is stirred at room temperature for 18 hours, treated with 200 cm³ of an aqueous saturated solution of ammonium chloride and taken up in 200 cm³ of ethyl ether and 200 g of ice. The organic phase is separated by settling, dried over magnesium sulphate, filtered and concentrated to dryness under reduced pressure (2.7 kPa). The residue is crystallized from 250 cm³ of petroleum ether and then recrystallized from 200 cm³ of methanol; the crystals are washed with 200 cm³ of isopropyl ether. 16.4 g of (3aRS, 4RS,5RS,7aRS)-2-benzyl- 7,7-diphenyl-4- ( 2-methoxyphenyl)perhydroisoindole-4,5-diol which melts at 236° C. are obtained.

Example 34

( 3aRS, 4RS, 5RS, 7aRS ) -7,7-Diphenyl-4- ( 2-methoxyphenyl)-2-[(2-benzyloxyphenyl )acetyl]perhydroisoindole-4,5-diol can be prepared in accordance with the operating method of Example 33, starting from 1.24 g of ( 3aRS, 4RS, 5RS, 7aRS ) -7,7-diphenyl-4- ( 2-methoxyphenyl ) perhydroisoindole-4,5-diol and 0.8 g of ( 2-benzyloxy ) phenylacetic acid. 1.7 g of ( 3aRS, 4RS, 5RS, 7aRS ) -7,7-diphenyl-4- ( 2-methoxyphenyl ) -2-[ (2-benzyloxyphenyl )acetyl]perhydroisoindole-4,5-diol which melts at 158° C. are obtained.

A mixture of 1.5 g of ( 3aRS, 4RS, 5RS, 7aRS )-7,7-diphenyl-4-(2-methoxyphenyl )-2-[ (2-benzyloxyphenyl)acetyl]perhydroisoindole-4,5-diol and 50 cm³ of ethanol is heated at 60° C. while stirring; 0.5 g of 20% strength palladium hydroxide-on-charcoal is added and the reaction mixture is then hydrogenated at a temperature of 60° C. and under atmospheric pressure, while stirring. After a reaction time of 45 minutes, the theoretical volume of hydrogen was absorbed; the reaction mixture is filtered and then concentrated to dryness under reduced pressure (2.7 kPa). The residue is crystallized from 20 cm³ of isopropyl ether. 0.8 g of ( 3aRS, 4RS, 5RS, 7aRS ) -7,7-diphenyl-4- (2-methoxyphenyl )-2-[(2-hydroxyphenyl)acetyl] perhydroisoindole-4,5-diol which melts at 188°–190° C. is obtained.

Example 35

By working in accordance with the operating method of Example 21, starting from 0.62 g of (3aRS,4RS,5RS,7aRS)-7,7-diphenyl-4-(2-methoxyphenyl)perhydroisoindole-4,5-diol and 0.30 g of (2-dimehylamino)phenylacetic acid, 0.47 g of (3aRS,4RS,5RS,7aRS)- 7,7-diphenyl-4-(2-methoxyphenyl)-2-[(2-dimethylaminophenyl)acetyl] perhydroisoindole-4,5-diol which melts at 250° C. is obtained.

Example 36

By working in accordance with the operating method of Example 21, starting from 1.04 g of (3AS,4S,5S,7AS)-7,7-diphenyl-4-(2-methoxyphenyl)perhydroisoindole-4,5-diol and 0.49 g of 3-indolylacetic acid, 1.25 g of (3AS,4S,5S, 7AS)-7,7-diphenyl-4-( 2-methoxyphenyl)-2-(3-indolylacetyl)perhydroisoindole-4,5-diol which melts at 210° C. are obtained.

Example 37

By working in accordance with the operating method of Example 21, starting from 0.62 g of (3aRS,4RS,5RS,7aRS)-7,7-diphenyl-4-(2-methoxyphenyl)perhydroisoindole-4,5-diol and 0.31 g of 3-(N-methylindolyl)acetic acid, 0.55 g of (3aRS,4RS,5RS,7aRS)-7,7-diphenyl-4-(2-methoxyphenyl)-2-[(N-methyl-3-indolyl)acetyl]perhydroisoindole-4,5-diol which melts at 240° C. is obtained.

Example 38

A suspension of 2-methoxyphenylmagnesium bromide (prepared starting from 14 cm³ of 2-bromoanisole and 2.8 g of magnesium) in 50 cm³ of anhydrous tetrahydrofuran is added dropwise to a suspension of 6.4 g of (3AS,7AS)-7, 7-diphenyl-2-[(S)-2-(2methoxyphenyl)propionyl] perhydroisoindol-4-one and 8.7 g of anhydrous cerium chloride in 250 cm³ of anhydrous tetrahydrofuran at room temperature, while stirring. The suspension is stirred at room temperature for 20 hours and then refluxed for 6 hours. After cooling, the reaction mixture is treated with an aqueous saturated solution of ammonium chloride, diluted with 500 cm³ of ethyl acetate, washed with 100 cm³ of water and then with 100 cm³ of an aqueous saturated solution of sodium chloride (twice), and is dried over magnesium sulphate, filtered and concentrated to dryness under reduced pressure (2.7 kPa). The residue is chromatographed on a Merck silica gel column (particle size 0.04–0.06 mm, diameter 5 cm, height 40 cm) by eluting under a pressure of 0.5 bar of nitrogen with a mixture of cyclohexane and ethyl acetate (80/20 by volume) and collecting fractions of 100 cm³. Fractions 16 to 26 are combined and then concentrated to dryness under reduced pressure (2.7 kPa). The residue is crystallized from a mixture of acetonitrile and diisopropyl ether. 1.83 g of (3AS,4S,7AS)-7,7-diphenyl-4-(2-methoxyphenyl)-2-[(S)-2-(2-methoxyphenyl)propionyl] perhydroisoindol-4-ol are obtained in the form of white crystals which melt at 244° C.

(3AS,7AS)-7,7-Diphenyl-2-[(S)-2-(2-methoxyphenyl)propionyl] perhydroisoindol-4-one can be prepared in the following manner:

0.46 g of 1-hydroxybenzotriazole and 7.07 g of (S)-2-(2-methoxyphenyl)propionic acid are added to a solution of 9.85 g of (3AS,7AS)-7,7-diphenylperhydroisoindol-4-one in 120 cm³ of dry dichloromethane, this solution is subsequently cooled to +5° C. and a suspension of 7.91 g of 1-(3-dimethylamino-propyl)-3-ethylcarbodiimide hydrochloride in 130 cm³ of dry dichloromethane is quickly added. The reaction mixture is stirred at +5° C. for 2 hours and at room temperature for 2 hours, washed with 50 cm³ of water and then washed with 50 cm³ of an aqueous saturated solution of sodium chloride (twice), and is dried over magnesium sulphate and concentrated to dryness under reduced pressure (2.7 kPa). The residue is chromatographed on a Merck silica gel column (particle size 0.04–0.06 mm, diameter 6 cm, height 30 cm) by eluting under a pressure of 0.5 bar of nitrogen with a mixture of cyclohexane and ethyl acetate (80/20 by volume) and collecting fractions of 50 cm³. Fractions 36 to 60 are combined and concentrated to dryness under reduced pressure (2.7 kPa). 12.3 g of (3AS, 7AS)-7,7-diphenyl-2-[(S)-2-(2methoxyphenyl)propionyl] perhydroisoindol-4-one are obtained in the form of a white solid.

Proton NMR spectrum (DMSO de): At room temperature, a mixture of the two rotamers is found: 1.13 and 1.23 (2d, J=7.5, 3H in total, —CH₃); 1.9 to 2.3 (mt, 2H, —CH₂— in 5); 2.6 to 4.2 (mt, —CH₂— and —CH); 3.36 and 3.86 (2s, 3H in total, —OCH₃); 6.7 to 7.7 (mt, 14H, aromatic).

Example 39

A solution of phenylmagnesium bromide (prepared starting from 3.14 g of bromobenzene and 0.48 [lacuna] of magnesium in 30 cm³ of ether) is added to a suspension of 4.09 g of (3aRS,7aRS)-7,7-diphenyl- 2-phenylacetylperhydroisoindol-4-one in 50 cm³ of tetrahydrofuran. The reaction mixture is stirred at 25° C. for 1 hour and then heated under reflux for 2.5 hours, cooled and treated with 150 cm³ of a saturated solution of ammonium chloride. The organic phase is washed with water (2×100 cm³). The aqueous phases are extracted with 100 cm³ of ethyl acetate. The combined organic phases are washed with 100 cm³ of a saturated solution of sodium chloride, dried over magnesium sulphate and concentrated to dryness under reduced pressure (2.7 kPa). The residue is crystallized in 30 cm³ of acetonitrile to give 2.9 g of (3aRS,4RS,7aRS)-2-phenylacetyl-4,7,7-triphenylperhydroisoindol-4-ol in the form of white crystals which melt at 270° C.

Example 40

A solution of 7.0 g of (3aRS,7aRS)-2-(3-indolylacetyl)-7,7-diphenylperhydroisoindol-4-one in 50 cm³ of tetrahydrofuran is added dropwise to a suspension of phenylmagnesium bromide (prepared starting from 4.7 cm³ of bromobenzene and 1.1 g of magnesium) in 40 cm³ of ethyl ether at 5° C. in the course of 20 minutes. The reaction mixture is stirred at room temperature for 4 hours, treated with 100 cm³ of an aqueous saturated solution of ammonium chloride and extracted with three times 150 cm³ of ethyl acetate. The organic solution is washed with 200 cm³ of an aqueous saturated solution of sodium chloride, and is dried over magnesium sulphate, filtered and concentrated to dryness under reduced pressure (2.7 kPa). The residue is chromatographed on a Merck silica gel column (particle size 0.06–0.20 mm, diameter 4 cm, height 30 cm) by eluting under a pressure of 0.5 bar of nitrogen with a mixture of cyclohexane and ethyl acetate (60/40 by volume) and collecting fractions of 100 cm³. After concentration under reduced pressure (2.7 kPa), 6.6 g of (3aRS,4RS,7aRS)-2-(3-indolylacetyl)- 4,7,7-triphenylperhydroisoindol-4-ol are obtained in the form of a white solid which melts at 187° C.

The present invention also relates to pharmaceutical compositions composed of a product of the general formula (I) or a salt, where these exist, if appropriate in combination with any other pharmaceutically compatible product, which may be inert or physiologically active. The compositions according to the invention can be used parenterally, orally, sublingually, rectally, topically, occularly, intranasally or in aerosols with a pulmonary target.

The sterile compositions for parenteral administration, which can be used, in particular, in the form of perfusions, are preferably aqueous or non-aqueous solutions, or suspensions or emulsions. Water, propylene glycol, a polyethylene glycol, vegetable oils, in particular olive oil, injectable organic esters, for example ethyl oleate, or other suitable organic solvents can be used as the solvent or vehicle. These compositions may also contain adjuvants, in particular wetting, isotonicizing, emulsifying, dispersing and stabilizing agents. The sterilization can be carried out in several ways, for example by aseptic filtration, by incorporating sterilizing agents into the composition, by irradiation or by heating. They may also be prepared in the form of solid sterile compositions which can be dissolved in a sterile injectable medium at the time of use.

The compositions for rectal administration are suppositories or rectal capsules which contain, in addition to the active product, excipients such as cocoa butter, semisynthetic glycerides or polyethylene glycols.

Solid compositions for oral administration which may be used are tablets, pills, powders or granules. In these compositions, the active product according to the invention (if appropriate combined with another pharmaceutically compatible product) is mixed with one or more inert diluents or adjuvants, such as sucrose, lactose or starch. These compositions can also comprise substances other than the diluents, for example a lubricating agent, such as magnesium stearate.

Liquid compositions for oral administration which can be used are solutions, suspensions, syrups, elixirs and pharmaceutically acceptable emulsions containing inert diluents, such as water or paraffin oil. These compositions can also comprise substances other than the diluents, for example wetting, sweetening or flavouring products.

The compositions for topical administration can be, for example, creams, ointments or lotions.

The compositions for occular administration can be instillations.

The compositions for intranasal administration can be pharmaceutically acceptable solutions or powders intended as drops or as sprays.

The compositions can also be aerosols. For use in the form of liquid aerosols, the compositions can be sterile stable solutions or solid compositions dissolved in sterile apyrogenic water, serum or any other pharmaceutically acceptable vehicle at the time of use. For use in the form of dry aerosols intended to be inhaled directly, the active principle is is finely divided and combined with a solid water-soluble diluent or vehicle having a particle size of 30 to 80 μm, for example dextran, mannitol or lactose.

In human therapy, the products according to the invention may be particularly useful in the treatment of pain of traumatic, post-surgical, menstrual or cephalic origin, in vascular pain of the face (cluster headache) and in treatments for migraine. The new isoindole derivatives are also useful in the treatment of inflammation in rheumatology, in the treatment of rheumatoid arthritis and for disturbances due to disregulation of the immune system, in treatments of inflammations in dermatology, such as psoriasis, herpes, urticaria, eczema, photodermatosis and burns, and in the case of dental or occular inflammatory disorders, and in the field of lachrymal secretions; they are also useful in treatments of spasmodic, painful and inflammatory symptoms of the digestive tract (ulcerative colitis, irritable bowel syndrome, Crohn's disease), the urinary tract (urinary hyperreflexia, cystitis) and respiratory tract (asthma, bronchial hypersecretion, chronic bronchitis, rhinitis). The products according to the invention can also be used in treatments of neurological diseases, Parkinson's disease and Alzheimer's disease, in treatments of inflammatory and/or autoimmune and/or demyelinizing diseases of the central and/or peripheral nervous system (plaque sclerosis, Guillain-Barré's syndrome, encephalopathies of viral origin and the like), for neurological syndromes in relation to plasma extravasation (oedema of the spinal cord, cerebral oedema and the like) or in relation to impairment of the haematoencephalic barrier, or for any spastic neurological syndrome (muscle-relaxing treatments). The products according to the invention can also be useful in treatments for anxiety, psychoses and schizophrenia, or else in treatments for cardiovascular disorders, such as hypotension. Another application may also be the treatment of gynaecological disorders, treatment of disorders associated with poor regulation of growth (dwarfism, hypotrophies secondary to chronic diseases in children, osteoporosis, development of grafts).

The doses depend on the required effect and on the duration of treatment. For an adult, they are generally between 0.25 and 1500 mg per day in staggered intake.

Generally, the doctor will determine the dosage which he considers to be the most suitable according to the age, weight and any other factors peculiar to the subject to be treated.

The following example, given nonlimitatively, illustrates a composition according to the invention.

Example

Tablets of active product having the following composition are prepared by the usual technique:

| | |
|---|---|
| (3aS, 4S, 7aS)-7,7-diphenyl-4-(2-methoxy-phenyl)-2-[(S)-2-(2-methoxyphenyl)-propionyl]perhydroisoindol-4-ol | 25 mg |
| starch | 83 mg |
| silica | 30 mg |
| magnesium stearate | 3 mg |

Although the invention has been described in conjunction with specific embodiments, it is evident that many alternatives and variations will be apparent to those skilled in the art in light of the foregoing description.

What is claimed is:

1. A perhydroisoindole derivative of formula:

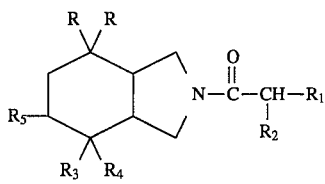

in which
the symbols R are identical and represent phenyl radicals which are optionally substituted by a halogen atom or by a methyl radical in position 2 or 3,
the symbol $R_1$ represents a phenyl radical which is optionally substituted by: (1) one or more halogen atoms, (2) hydroxyl; (3) an alkyl radical, which optionally is substituted by halogen atoms or amino, alkylamino or dialkylamino radicals; (4) an alkyloxy or (5) alkylthio radical, which optionally is substituted by hydroxyl radicals, amino radicals, alkylamino radicals or dialkylamino radicals which optionally are substituted by phenyl, hydroxyl, amino, or dialkylamino radicals, the alkyl parts of which, with the nitrogen atom to which they are attached, form a heterocycle having 5 to 6 chain members which may contain another heteroatom selected from oxygen, sulphur or nitrogen and optionally substituted by an alkyl, hydroxyl or hydroxyalkyl radical; or the phenyl radical is substituted by amino radicals, alkylamino radicals or dialkylamino radicals, the alkyl parts of which, with the nitrogen atom to which they are attached, optionally form a heterocycle as defined above, or $R_1$ is selected from a cyclohexadienyl radical, naphthyl radical, indenyl radical or mono- or polycyclic, saturated or unsaturated, heterocyclyl radical containing 5 to 9 carbon atoms and one or more heteroatoms selected from oxygen, nitrogen or sulphur, which is optionally substituted by a halogen atom or by an alkyl or alkyloxy radical, the symbol $R_2$ represents hydrogen, halogen, hydroxyl, alkyl, aminoalkyl, alkylaminoalkyl, dialkylaminoalkyl, alkyloxy, alkylthio, acyloxy, carboxyl, alkyloxycarbonyl, dialkylaminoalkyloxy-carbonyl, benzyloxycarbonyl, amino or acylamino, the symbol $R_3$ represents a phenyl radical which is optionally substituted in position 2 by an alkyl or alkyloxy radical containing 1 or 2 carbon atoms and the symbol $R_4$ represents a fluorine atom or a hydroxyl radical, the symbol $R_5$ represents a hydrogen atom, hydroxyl radical or forms a bond with $R_4$ provided that $R_4$ is not fluorine when $R_5$ is hydroxy, said radicals being in the racemic form, in its stereoisomer forms having the structure:

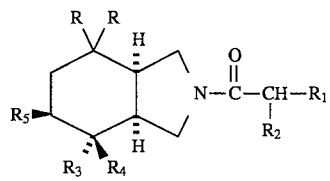

in its (R) or (S) forms on the —$CHR_1R_2$ chain, or in the form of the mixture of several of these forms, and its salts, where these exist.

2. A perhydroisoindole derivative according to claim 1, wherein the symbol $R_1$ is a mono- or polycyclic, saturated or unsaturated, heterocyclyl radical selected from thienyl, furyl, pyridyl, dithiinyl, indolyl, isoindolyl, benzothienyl, thiazolyl, isothiazolyl, oxazolyl, imidazolyl, pyrrolyl, triazolyl, thiadiazolyl, quinolyl, isoquinolyl and naphthyridinyl.

3. A perhydroisoindole derivative according to claim 1, wherein:
the symbol $R_1$ represents a phenyl radical which is optionally substituted by one or more hydroxyl, alkyloxy or dialkylamino radicals, naphthyl radical, indenyl radical or mono- or polycyclic heterocyclyl radical selected from thienyl, indolyl and benzothienyl and optionally substituted by a halogen atom or by an alkyl or alkyloxy radical, the symbol $R_2$ represents a hydrogen atom or a hydroxyl, alkyl or amino radical, the symbol $R_3$ represents a phenyl radical which is optionally substituted in position 2 by an alkyl or alkyloxy radical containing 1 or 2 carbon atoms and the symbol $R_4$ represents a fluorine atom or a hydroxyl radical, the symbol $R_5$ represents a hydrogen atom, hydroxyl radical or forms a bond with $R_4$ provided that $R_4$ is not fluorine when $R_5$ is a hydroxyl radical.

4. A perhydroisoindole derivative selected from the group consisting of 7,7-diphenyl-4-( 2-methoxyphenyl)-2-[2-(2-methoxyphenyl)propionyl]perhydroisoindol-4-ol; 7,7-diphenyl-4-(2-methoxyphenyl)-2-[2-(2-methoxyphenyl)propionyl]perhydroisoindole-4,5-diol; 7,7-diphenyl-4-(2-methoxyphenyl)-2-[2-(2-hydroxyphenyl)acetyl] perhydroisoindol-4-ol; 7,7-diphenyl-4-(2-methoxyphenyl)-2-(3-indolylacetyl)perhydroisoindole- 4,5-diol; 7,7-diphenyl-4-(2-methoxyphenyl)-2-[(2methoxyphenyl)acetyl] perhydroisoindol-4-ol; or 7,7-diphenyl-4-(2-methoxyphenyl)-2-[2-(2-hydroxyphenyl)propionyl] perhydroisoindol-4-ol.

5. Pharmaceutical composition comprising at least one product according to claim 1 in the pure state or in the form of a combination with one or more compatible and pharmaceutically acceptable adjuvants or diluents.

* * * * *